United States Patent
Shia et al.

(10) Patent No.: US 12,329,354 B2
(45) Date of Patent: Jun. 17, 2025

(54) ANTITWIST MECHANISM FOR ROBOTIC ENDOSCOPE CAMERA

(71) Applicants: CANON U.S.A., INC., Melville, NY (US); Canon Kabushiki Kaisha, Tokyo (JP)

(72) Inventors: Benedict Shia, Needham, MA (US); Junichi Matsumura, Shizuoka (JP); Takahisa Kato, Brookline, MA (US)

(73) Assignees: Canon U.S.A, Inc., Melville, NY (US); Canon Kabushiki Kaisha, Tokyo (JP)

(*) Notice: Subject to any disclaimer, the term of this patent is extended or adjusted under 35 U.S.C. 154(b) by 568 days.

(21) Appl. No.: 17/591,432

(22) Filed: Feb. 2, 2022

(65) Prior Publication Data
US 2023/0240513 A1 Aug. 3, 2023

(51) Int. Cl.
*A61B 1/00* (2006.01)
*A61B 1/005* (2006.01)
*A61B 1/018* (2006.01)
*A61B 1/05* (2006.01)

(52) U.S. Cl.
CPC .......... *A61B 1/0008* (2013.01); *A61B 1/0055* (2013.01); *A61B 1/0057* (2013.01); *A61B 1/018* (2013.01); *A61B 1/05* (2013.01)

(58) Field of Classification Search
CPC ... A61B 1/0008; A61B 1/0055; A61B 1/0057; A61B 1/018; A61B 1/05; A61B 1/051; A61B 1/00098; H04N 23/51–55
See application file for complete search history.

(56) References Cited

U.S. PATENT DOCUMENTS

| | | | |
|---|---|---|---|
| 5,337,734 A | 8/1994 | Saab | |
| 5,438,975 A * | 8/1995 | Miyagi | A61B 1/00071 600/141 |
| 8,864,652 B2 | 10/2014 | Diolaiti et al. | |
| 9,572,628 B2 | 2/2017 | Zubiate et al. | |
| 10,111,723 B2 | 10/2018 | Olson | |
| 10,275,899 B2 | 4/2019 | Geissler et al. | |
| 10,376,134 B2 | 8/2019 | Schlessginer et al. | |

(Continued)

FOREIGN PATENT DOCUMENTS

| | | |
|---|---|---|
| JP | S57-122812 U | 7/1982 |
| JP | 2014-200871 A | 10/2014 |
| JP | 2014-533996 A | 12/2014 |

*Primary Examiner* — John P Leubecker
*Assistant Examiner* — Li-Ting Song
(74) *Attorney, Agent, or Firm* — Canon U.S.A., Inc., IP Division

(57) ABSTRACT

A steerable catheter driven by a robotic controller comprises: a catheter body having a catheter tip and tool channel which spans from a proximal end of the catheter body and through the catheter tip along a catheter axis. The catheter tip includes a ramp-like surface formed inside part of the tool channel diameter. The ramp-like surface is an inclined flat surface formed at an angle with respect to a plane parallel to the catheter axis, such that the angle increases as the ramp-like surface spans from distal end towards the proximal end of the catheter tip. A housing mechanism permanently attached to an imaging device is configured to lock the imaging device to the ramp-like surface so as to prevent rotation of the imaging device with respect to the tool channel and/or prevent twisting of the catheter tip with respect to the imaging device.

25 Claims, 8 Drawing Sheets

(56) References Cited

U.S. PATENT DOCUMENTS

| | | |
|---|---|---|
| 10,624,701 B2 | 4/2020 | Hunter et al. |
| 2003/0028100 A1 | 2/2003 | Tearney et al. |
| 2003/0163128 A1 | 8/2003 | Patil et al. |
| 2005/0273090 A1 | 12/2005 | Nieman et al. |
| 2007/0177008 A1* | 8/2007 | Bayer ................ A61B 1/00096 348/65 |
| 2008/0117292 A1* | 5/2008 | Orihara ................ H04N 23/55 348/E5.026 |
| 2009/0253955 A1* | 10/2009 | Akiba ................ A61B 1/053 600/109 |
| 2011/0026787 A1 | 2/2011 | Hale et al. |
| 2011/0245610 A1 | 10/2011 | Tanaka |
| 2012/0065469 A1* | 3/2012 | Allyn ................ A61B 1/2736 600/109 |
| 2013/0204126 A1 | 8/2013 | Namati et al. |
| 2017/0296038 A1* | 10/2017 | Gordon ............ A61B 1/00091 |
| 2019/0261946 A1* | 8/2019 | Panzenbeck ........ A61B 8/0891 |
| 2020/0305699 A1 | 10/2020 | Herriges |
| 2021/0382293 A1* | 12/2021 | Kodama ................ H04N 23/57 |
| 2022/0346637 A1* | 11/2022 | Yeung ................ A61B 1/00098 |
| 2022/0369918 A1* | 11/2022 | Toth ................ A61B 1/00009 |
| 2022/0409854 A1* | 12/2022 | Gao ................ A61B 1/0052 |
| 2023/0164418 A1* | 5/2023 | Sgarz ................ A61B 1/00096 348/65 |

\* cited by examiner

Cross-section A-A

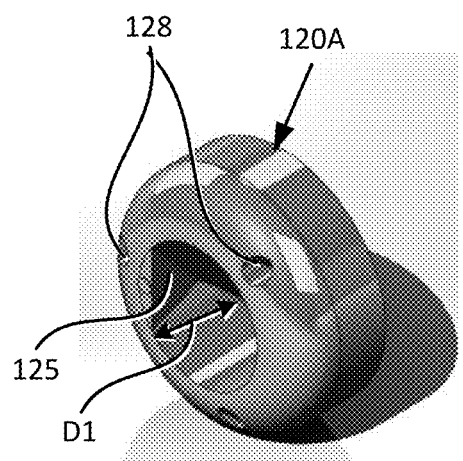
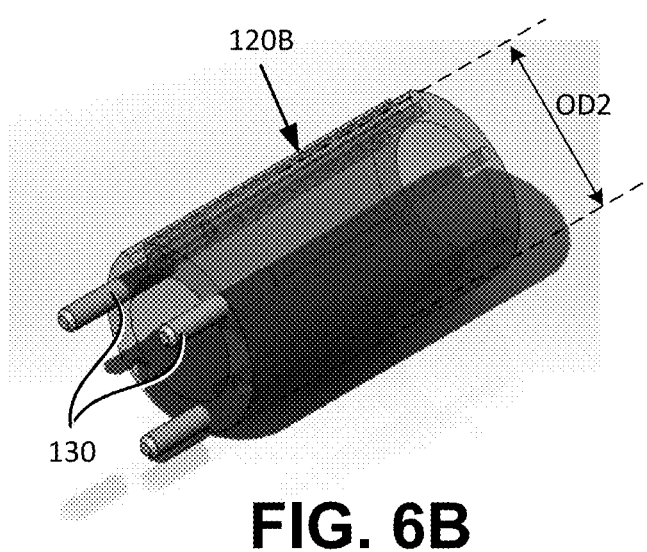
FIG. 6A
FIG. 6B
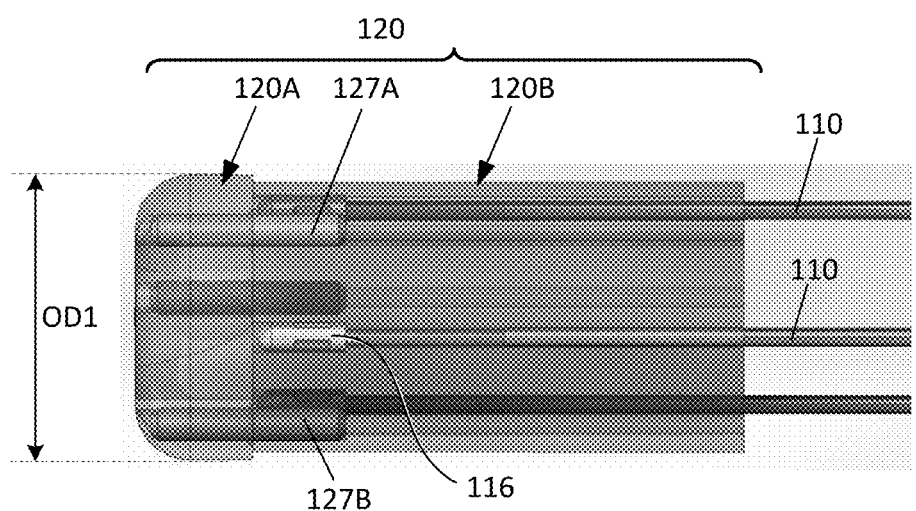
FIG. 6C

ANTITWIST MECHANISM FOR ROBOTIC ENDOSCOPE CAMERA

CROSS-REFERENCE TO RELATED APPLICATIONS n/a

BACKGROUND INFORMATION

Field of Disclosure

The present disclosure relates to medical devices. More particularly, the disclosure is directed to various embodiments of an anti-twist mechanism for robotic catheters or endoscopes. The anti-twist mechanism is configured to prevent rotation of removable imaging device such as a camera with respect a tool channel of the catheter or endoscope.

Description of Related Art

Robotic catheters or endoscopes include a flexible tubular shaft operated by an actuating force (pulling or pushing force) applied through metallic wires controlled by an actuator unit. The flexible tubular shaft (herein referred to as a "steerable catheter") may include multiple articulated sections configured to continuously bend and turn in a snake-like fashion. Typically, the steerable catheter is inserted through a natural orifice or small incision of a patient's body, and is deployed through a patient's lumen to a target site, for example, a site within the patient's anatomy designated for an intraluminal procedure, such as ablation or biopsy. A handheld controller (e.g., a gamepad controller) is used as an interface for interaction between the user and the robotic system to control endoscope navigation within the patient's body.

The navigation of the steerable catheter is guided by a camera or videoscope arranged at the distal tip of the catheter shaft. A display device, such as a liquid crystal display (LDC) monitor provided in a console or attached to a wall, displays an image of the camera's field of view (FOV image) to assist the user in navigating the steerable catheter through the patient's anatomy to reach the target site. The orientation of the camera view, the controller, and the catheter is mapped (calibrated) before inserting the catheter into the patient's body. As the user manipulates the endoscope inside the patient's anatomy, the camera transfers the camera's FOV image to the display device. Ideally, the displayed image should allow the user to relate to the endoscopic image as if the user's own eyes were actually inside the endoscope cavity.

However, during navigation, the distal tip of the steerable catheter can twist causing the camera to rotate, resulting in errors in the correlation of steering inputs to visual guidance. Twisting of a robotic catheter can occur due to several factors, for example, as described in U.S. Pat. No. 9,572,628 which is incorporated by reference herein in its entirety. In the state of the art, numerous publications have disclosed techniques to maintain the proper upright gravity-leveled orientation of the endoscopic image regardless of how the steerable device is manipulated. Techniques for controlling rotation of the displayed image include measuring the orientation of the endoscope, and then rotating the endoscopic image optically, mechanically or electronically to compensate for the change in orientation of the endoscope tip or rotation of the camera. See, fore example, patent application publications US 2011/0026787, US 2013/0204126, and patent publications U.S. Pat. Nos. 8,864,652, 10,275,899 and 10,376,134.

A new type of steerable catheter known as a Medical Continuum Robot (MCR) is designed to have a reduced number of channels (preferably a single channel) through which a flexible videoscope camera is inserted to provide image guidance during navigation, and the same channel is used to allow access for surgical instruments, end effectors, and/or to allow passage of fluids. The use of a single channel for the imaging device and for tools allows for a smaller overall profile than conventional endoscope devices where the camera is integrated into the catheter tip, and separate channels are used to allow access for tools and fluids.

In the catheter device for an MCR, since the camera is not fixed to the catheter tip, the passage of fluids can be performed with the camera in place, by providing a certain tolerance (a gap) between the camera and the inner diameter (ID) of the catheter's channel. For example, during imaging, the gap is used to supply water through the catheter to clean mucus or blood blocking the camera view. However, the steerable catheter has multiple bending sections, and each bending section is manipulated by one or more drive wires that steer the catheter through tortuous anatomies. Pulling and/or pushing on the drive wires causes length changes (displacement) in the wires within the catheter. These changes cause the individual bending sections to deflect the steerable catheter with three or more degrees of freedom (DOF). The drive wire or wires being pulled bend to form an inner bend radius, and the wire or wires that are pushed bend along an outer bend radius.

Due to the structure of the bending section, the catheter can twist due to the actuation inputs and due to friction with the anatomy through which the catheter navigates. Since the camera is not secured to the tip of the catheter, the tip is free to twist or rotate around the camera. Alternatively, the camera may rotate with respect to the catheter body when the tip of the catheter bends and/or moves. The twisting or rotation of the catheter tip around the camera results in a discrepancy between the view of the camera and the steering inputs provided at the proximal end of the catheter through the controller. Therefore, there is a need for an improved catheter structure which can prevent negative effects of camera rotation, while maintaining appropriate correlation between the orientation of the camera view, the orientation of the gamepad controller, and the orientation of the catheter tip.

SUMMARY OF EXEMPLARY EMBODIMENTS

According to at least one embodiment disclosed herein, there is provided a steerable catheter configured to be driven by a medical continuum robot (MCR). The steerable catheter includes a catheter body having at least one tool channel spanning from a proximal end to a distal end of the catheter body, and a plurality of drive wires arranged along the wall of the tool channel. The tool channel is configured to pass there-through one or more of a medical tool, an imaging device, and a fluid. Anti-twist features are provided in the catheter tip or in the imaging device to removably lock the imaging device to the catheter tip. When one or more of the drive wires transfers an actuating force from an actuator unit to the catheter body, at least a portion of the catheter body is bent and/or rotated, while the anti-twist mechanism prevents rotation of an imaging device within the tool channel.

The anti-twist features include a ramp-like surface built into the catheter tip, and a housing mechanism permanently attached to the endoscope camera. The ramp-like surface produces a simple geometry with minimal impact on the cross sectional area of the tool channel, providing adequate fluid flow and the ability to pass instruments easily out the catheter tip past the anti-twist mechanism.

A steerable catheter driven by a robotic controller comprises: a catheter body having a catheter tip and tool channel which spans from a proximal end of the catheter body and through the catheter tip along a catheter axis. The catheter tip a ramp-like surface formed in part of the tool channel diameter. The ramp-like surface is an inclined flat surface formed at an angle with respect to a plane parallel to the catheter axis, such that the angle increases as the ramp-like surface spans from distal end towards the proximal end of the catheter tip. A housing mechanism permanently attached to an imaging device is configured to lock the imaging device to the ramp-like surface so as to prevent rotation of the imaging device with respect to the tool channel and/or prevent twisting of the catheter tip with respect to the imaging device.

These and other objectives, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

FIG. 6A, FIG. 6B and FIG. 6C shows isometric views of the two-part catheter tip 120 corresponding to the embodiment shown in FIG. 4D.

DETAILED DESCRIPTION OF EXEMPLARY EMBODIMENTS

Figure 1A:
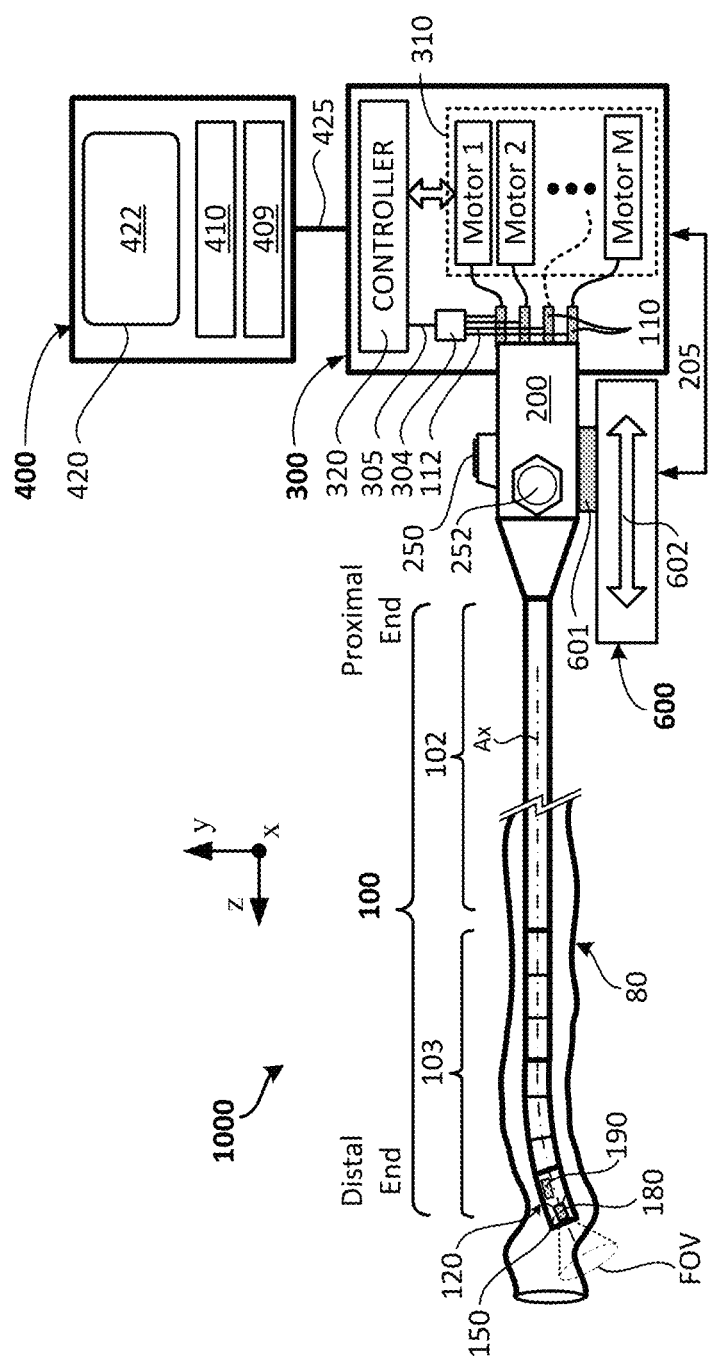
FIG. 1A shows an embodiment of the continuum robot system 1000 configured to operate a steerable catheter 100.

Aspects of the present disclosure are best understood by reading the following detailed description in light of the accompanying figures. It is noted that, in accordance with the standard practice, the various features of the drawings are not drawn to scale and to not represent actual components. Several details such as dimensions of the various features may be arbitrarily increased or reduced for ease of illustration. In addition, reference numerals and/or letters are repeated in the various examples to depict similar components and/or functionality. This repetition is for the purpose of simplicity and clarity and does not in itself limit the various embodiments and/or configurations the same components discussed.

Throughout the figures, the same reference numerals and characters, unless otherwise stated, are used to denote like features, elements, components or portions of the illustrated embodiments. In addition, while the subject disclosure is described in detail with reference to the enclosed figures, it is done so in connection with illustrative exemplary embodiments. It is intended that changes and modifications can be made to the described exemplary embodiments without departing from the true scope of the subject disclosure as defined by the appended claims. Although the drawings represent some possible configurations and approaches, the drawings are not necessarily to scale and certain features may be exaggerated, removed, or partially sectioned to better illustrate and explain certain aspects of the present disclosure. The descriptions set forth herein are not intended to be exhaustive or otherwise limit or restrict the claims to the precise forms and configurations shown in the drawings and disclosed in the following detailed description.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached", "coupled" or the like to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown in one embodiment can apply to other embodiments. It will also be appreciated by those of skill in the art that references to a structure or feature that is disposed "adjacent" to another feature may have portions that overlap or underlie the adjacent feature.

The terms first, second, third, etc. may be used herein to describe various elements, components, regions, parts and/or sections. It should be understood that these elements, components, regions, parts and/or sections are not limited by these terms of designation. These terms of designation have been used only to distinguish one element, component, region, part, or section from another region, part, or section. Thus, a first element, component, region, part, or section discussed below could be termed a second element, component, region, part, or section merely for purposes of distinction but without limitation and without departing from structural or functional meaning.

As used herein, the singular forms "a", "an", and "the" are intended to include the plural forms as well, unless the context clearly indicates otherwise. It should be further understood that the terms "includes" and/or "including", "comprises" and/or "comprising", "consists" and/or "consisting" when used in the present specification and claims, specify the presence of stated features, integers, steps, operations, elements, and/or components, but do not preclude the presence or addition of one or more other features, integers, steps, operations, elements, components, and/or groups thereof not explicitly stated. Further, in the present disclosure, the transitional phrase "consisting of" excludes any element, step, or component not specified in the claim. It is further noted that some claims or some features of a claim may be drafted to exclude any optional element; such claims may use exclusive terminology as "solely," "only" and the like in connection with the recitation of claim elements, or it may use of a "negative" limitation.

The term "about" or "approximately" as used herein means, for example, within 10%, within 5%, or less. In some embodiments, the term "about" may mean within measurement error. In this regard, where described or claimed, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range, if recited herein, is intended to be inclusive of end values and includes all sub-ranges subsumed therein, unless specifically stated otherwise. As used herein, the term "substantially" is meant to allow for deviations from the descriptor that do not negatively affect the intended purpose. For example, deviations that are from limitations in measurements, differences within manufacture tolerance, or variations of less than 5% can be considered within the scope of substantially the same. The specified descriptor can be an absolute value (e.g. substantially spherical, substantially perpendicular, substantially concentric, etc.) or a relative term (e.g. substantially similar, substantially the same, etc.).

Unless specifically stated otherwise, as apparent from the following disclosure, it is understood that, throughout the disclosure, discussions using terms such as "processing," "computing," "calculating," "determining," "displaying," or the like, refer to the action and processes of a computer system, or similar electronic computing device, or data processing device that manipulates and transforms data represented as physical (electronic) quantities within the computer system's registers and memories into other data similarly represented as physical quantities within the computer system memories or registers or other such information storage, transmission or display devices. Computer or electronic operations described in the specification or recited in the appended claims may generally be performed in any order, unless context dictates otherwise. Also, although various operational flow diagrams are presented in a sequence(s), it should be understood that the various operations may be performed in other orders than those which are illustrated or claimed, or operations may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "in response to", "related to," "based on", or other like past-tense adjectives are generally not intended to exclude such variants, unless context dictates otherwise.

The present disclosure generally relates to medical devices, and it exemplifies embodiments of an endoscope or catheter, and more particular to a steerable catheter controlled by a medical continuum robot (MCR). The embodiments of the endoscope or catheter and portions thereof are described in terms of their state in a three-dimensional space. As used herein, the term "position" refers to the location of an object or a portion of an object in a three-dimensional space (e.g., three degrees of translational freedom along Cartesian X, Y, Z coordinates); the term "orientation" refers to the rotational placement of an object or a portion of an object (three degrees of rotational freedom—e.g., roll, pitch, and yaw); the term "posture" refers to the position of an object or a portion of an object in at least one degree of translational freedom and to the orientation of that object or portion of object in at least one degree of rotational freedom (up to six total degrees of freedom); the term "shape" refers to a set of posture, positions, and/or orientations measured along the elongated body of the object.

As it is known in the field of medical devices, the terms "proximal" and "distal" are used with reference to the manipulation of an end of an instrument extending from the user to a surgical or diagnostic site. In this regard, the term "proximal" refers to the portion (e.g., a handle) of the instrument closer to the user, and the term "distal" refers to the portion (tip) of the instrument further away from the user and closer to a surgical or diagnostic site. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

As used herein the term "catheter" generally refers to a flexible and thin tubular instrument made of medical grade material designed to be inserted through a narrow opening into an anatomical lumen (e.g., a vessel) to perform a broad range of medical functions. The more specific term "steerable catheter" refers to a medical instrument comprising an elongated shaft made of one or more actuatable sections.

As used herein the term "endoscope" refers to a rigid or flexible medical instrument which uses a camera or a fiber-based optical probe to look inside a body cavity or organ of a patient. A medical procedure in which an endoscope is inserted through a natural opening is called endoscopy. Specialized endoscopes are generally named for how or where the endoscope is intended to be used, such as the bronchoscope (mouth), sigmoidoscope (rectum), cystoscope (bladder), nephroscope (kidney), bronchoscope (bronchi), laryngoscope (larynx), otoscope (ear), arthroscope (joint), laparoscope (abdomen), and gastrointestinal endoscopes. In the present disclosure, the terms "optical fiber", "fiber optic", or simply "fiber" refers to an elongated, flexible, light conducting conduit capable of conducting light from one end to another end due to the effect known as total internal reflection. The terms "light guiding component" or "waveguide" may also refer to, or may have the functionality of, an optical fiber. The term "fiber" may refer to one or more light conducting fibers.

The term "twist" or "twisted" or "twisting" refers to an action to bend or rotate or turn something with a force (moment) in a circular motion with respect to a point of reference. The action of twisting something can cause a change in shape or position that is not normal. The term "conduit" is taken to mean a tubular structure such as a tube or pipe or channel or groove or a through used for passing or routing or protecting a wire. An example is a conduit for an electrical wire. In the present disclosure, conduits can be used for passing or routing or protecting or attaching a drive wire and/or electrical wire to the catheter.

<Continuum Robot System>

Figure 1B:
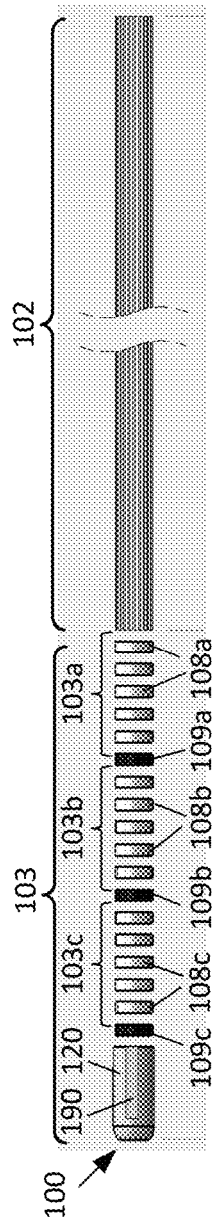
FIG. 1B shows an embodiment of the steerable catheter 100.
Figure 2A:
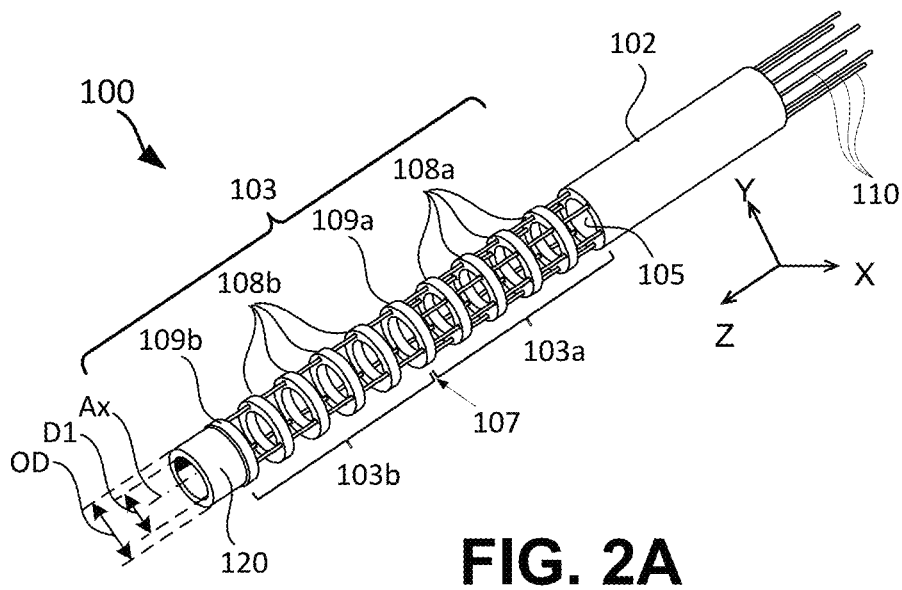
FIG. 2A, FIG. 2B, and FIG. 2C illustrate further details of the steerable catheter 100 having a catheter tip 120, according to an exemplary embodiment of the present disclosure.
Figure 2B:
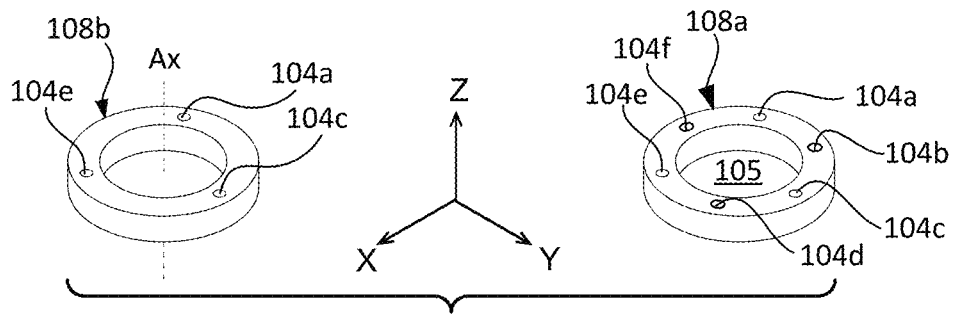
Figure 2C:
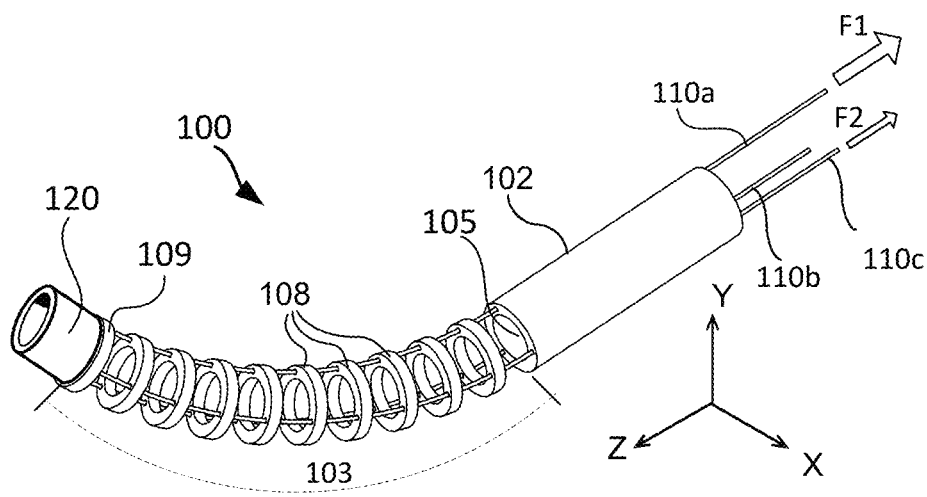

FIG. 1A through FIG. 2C show relevant parts of a continuum robot system 1000 configured to operate a robotic catheter or endoscope. FIG. 1A shows an embodiment of the continuum robot system 1000 configured to operate a steerable catheter 100. FIG. 1B shows an embodiment of the steerable catheter 100. FIG. 2A, FIG. 2B, and FIG. 2C illustrate one or more embodiments of the steerable catheter 100 and relevant components of an anti-twist feature provided in the tool channel of the catheter.

As shown in FIG. 1A, a general structure of the continuum robot system 1000 includes a computer system 400 (e.g., a system console), a robotic control system 300, and the steerable catheter 100 which is connected to the robotic control system 300 via a handle 200. In alternate applications or embodiments, the steerable catheter 100 can be connected via the handle 200 to a handheld controller such as a gamepad controller or a portable electronic device such as a smartphone or tablet computer. By convention, the system 1000 operates in a three-dimensional (3D) space defined by a 3D Cartesian coordinate system of x, y, z axes. The steerable catheter 100 includes a non-steerable proximal section 102, a steerable distal section 103 and a catheter tip 120 arranged along a longitudinal catheter axis Ax which is parallel to the z-axis direction. The distal section 103 is divided into multiple bending segments (103a, 103b, 103c), and each bending segment is composed of ring-shaped components (rings), and configured to be individually actuated (bent and/or rotated) by one or more drive wires 110. Within the catheter tip 120, an imaging device 180 is removably arranged by an anti-twist housing mechanism 150.

The bending and/or rotating during insertion/withdrawal of steerable catheter 100 (herein generally referred to as "steering") is controlled by a kinematic actuation system comprised of the handle 200, the robotic control system 300, and a controller (e.g., a gamepad controller or computer system 400). More specifically, the robotic control system 300 generally includes or is connected to a handheld controller and/or a control room computer. The computer system 400 along with suitable software, firmware, and peripheral hardware operated by one or more processors of a central processing unit (CPU) 410 represents a generalized controller system used to control steering of the steerable catheter 100. A memory module 409 represents computer-readable media that stores software applications and computer-executable code for operating the continuum robot system 1000 as whole. The computer system 400, the robotic control system 300, and the handle 200 are operably connected to each other by a network link (e.g., a wireless link) or a cable bundle 425. In some embodiments, the robotic control system 300 may be implemented by, or connected to, a handheld controller, such as a gamepad or a portable processing device like a smart phone or a tablet computer. Among other functions, the robotic control system 300 and/or computer system 400 can provide a surgeon or other user with a display screen 422 and/or graphical user interface (GUI) through an image display device 420. The image display device 420, which may include an LCD or OLED display, enables the user to observe images acquired by the imaging device 180, and interact with the steerable catheter 100 and the system 1000 as whole.

The handle 200 provides an electromechanical interface between the steerable catheter 100 and the robotic control system 300. For example, the handle 200 may provide an interface for mechanical, electrical, and/or optical connections, and a data or digital acquisition (DAQ) system for interfacing the steerable catheter 100 with the robotic control system 300. The handle 200 may also provide one or more access ports 250 that a surgeon or operator may use to insert end effector tools. The handle 200 may also include one or more dials 252 for manually connecting the catheter 100 to the system. The term "end effector" refers to a working part of a surgical instrument or tool. Endoscopic surgical tools may include clamps, graspers, scissors, staplers, needles, and other similar tools, which serve to manipulate body parts (organs or tissue) during examination or surgery, as it is known to persons of ordinary skill in the art. The handle 200 is attachable to a robotic support platform 600 (e.g., a linear stage 602 and/or robotic arm 601) to move the steerable catheter 100 in a linear direction. The robotic control system 300 and/or computer system 400 can send control signals to the support platform 600 and/or linear stage 601 via the handle 200 or/or through an additional connection 205 such as a wired or wireless network link.

The robotic control system 300 includes an actuator system 310 and a controller 320. The controller 320 may include a proportional-integral-derivative (PID) controller or other digital signal processor (DSP) along with suitable software, firmware and peripheral hardware, as it is known to persons having ordinary skill in the art. PID or DSP-based controllers are generally dedicated integrated circuits built into components of the robotic system 1000. However, in some embodiments, DSP functionality can also be implemented by other circuits, for example, by using field-programmable gate array chips (FPGAs) controlled by the computer system 400. The actuator system 310 may include a plurality of actuating motors (or actuators), which are shown in FIG. 1A as Motor 1, Motor 2, through Motor M. In some embodiments M can be equal to the number of drive wires 110 necessary for steering the various segments of the distal section 103. In other embodiments, more than one (or all) drive wires 110 can be actuated by a single motor or actuator. The drive wires 110 are typically metallic wires with one end anchored at anchor members along the length of the distal section 103 and another end connected to a motor or actuator of the actuator system 310.

The robotic control system 300 also includes one or more sensors 304 operatively connected to the drive wires 110 and/or to the steerable catheter 100 via electrical wires 112. Sensors 304 can include one or more strain sensors and/or one or more position/orientation sensors which serve to detect and/or measure compressive or tensile forces exerted be the actuator system 310 on the drive wires 110. The sensors 304 can output one or more than one signal 305 corresponding to an amount of compressive or tensile force (an amount of strain) being applied to each drive wire 110 at any given point in time. The signals 305 from the sensors 304 (strain sensor and/or position sensor) for each drive wire 110 are fed into the controller 320 to control the actuation of each drive wire individually by a feedback control loop. In this manner, each drive wire 110 can be actively controlled to implement appropriate shaft guidance for navigating the steerable catheter 100 through intraluminal tortuous paths of a patient's anatomy.

FIG. 1B shows an embodiment of the steerable catheter 100. The steerable catheter 100 has an elongated tubular shaft (a catheter body) also referred to as a tubular sleeve or tubular guide or tubular sheath. As already mentioned above, the steerable catheter 100 includes a proximal section 102 and a distal section 103. The distal section 103 includes a plurality of bending segments and a catheter tip 120 arranged at the fore of the most distal bending segment. The bending segments may include a first bending segment 103a composed of plural ring members 108a, a second bending segment 103b composed of plural ring members 108b, and a third bending segment 103c composed of plural ring members 108c. A plurality of drive wires 110 is arranged along (typically within) the wall of the catheter shaft. Drive wires 110 are anchored at anchoring members 109a, 109b, and 109c to actuate each bending segment individually and/or independently.

Along the catheter's length, there is at least one working channel spanning through the proximal end and through the distal end of the catheter body. The working channel will be referred to as a "tool channel" for simplicity. The tool channel 105 allows access for various interventional tools (end effectors) to be delivered from the access port 250 and beyond the catheter tip 120 of the steerable catheter 120. The tool channel 105 may also be used for sending or retrieving fluids in liquid or gaseous state (e.g., air or water) to a target region inside the patient. Furthermore, the tool channel 105 may be used for removably holding a medical imaging device 180, such as an endoscope camera, a videoscope, or a fiber-based imagining probe along with optical fibers and/or electric wires necessary for operating such devices. An example of an endoscope camera includes, but is not limited to, a chip-on-tip (COT) camera, such as a camera with a miniature CMOS sensor configured to be removably arranged at distal tip 120 of the steerable catheter 100. In addition, to track the position and orientation of the catheter, one or more electromagnetic (EM) sensors 190 can be provided in the distal tip 120 and/or along the length of the steerable catheter 100.

In operation, when the steerable catheter 100 is inserted through an anatomical lumen 80, the distal tip 120 is driven according to kinematic principles based on forces applied by the controller 320 to one or more of the bending segments via the drive wires 110. The segments of the distal section 103 can be controlled individually to direct the catheter tip 120 with a combined actuation of all bending segments, or the catheter tip can be operated in a follow-the-leader (FFL) approach by controlling the most distal being segment and the remaining segments following the path traced out by most distal segment. The imaging device 180 is generally assembled (inserted) into the catheter tip 120, prior to using the catheter in a patient. However, during navigation of the catheter through the lumen or during a procedure, the imaging device 180 can be withdrawn from the catheter body and reinserted through the tool channel 105.

FIG. 2A, FIG. 2B, and FIG. 2C illustrate further details of the steerable catheter 100, according to an exemplary embodiment of the present disclosure. FIG. 2A is a perspective view of the steerable catheter 100 comprising a proximal section 102, a distal section 103, and a catheter tip 120. FIG. 2B shows ring-shaped members (anchor member 109b and ring-shaped wire-guiding member 108a) of the distal section 103. FIG. 2C shows an actuated state of a steerable catheter 100.

As shown in FIG. 2A (similar to FIG. 1B), the proximal section 102 is shaped as a tubular shaft, and the distal section 103 includes a plurality of ring-shaped components arranged along a central longitudinal axis Ax which is parallel to the z-axis direction. A plurality of wires 110 are arranged along the wall of the tubular shaft and pass through wire-conduits 104 of the ring-shaped components (see FIG. 2B). The distal section 103 includes a plurality of bending segments, including a first bending segment 103a and a second bending segment 103b. The bending segments are joined to each other at an inflection point 107 by an anchor member 109a.

The first bending segment 103a includes a plurality of ring-shaped guide members 108a, and the second bending segment 103b includes a plurality of ring-shaped guide members 108b. The catheter tip 120 is arranged at the front of the most distal bending segment.

The plurality of drive wires 110 run along the wall of proximal section 102 and through one or more bending segments of the distal section 103. At the proximal end of the catheter, all drive wires 110 are coupled to individual motors or actuators of the actuator system 310 (as shown in FIG. 1A). In certain embodiments, one or more of the drive wires 110 may not be coupled to an actuator, but instead it may be attached to a fixed structure (e.g., a chassis or housing) of the robotic control system 300. In this case, the drive wires are not actuated, and serve as support wires for the steerable catheter 100.

Along the distal section 103, the drive wires 110 pass through the annular wall of the ring-shaped guide members 108 in a lengthwise direction. On the distal section 103, the drive wires 110 are selectively anchored to wire-anchoring components 109. Some drive wires 110 are anchored at the inflection point 107 to a first anchor member 109a, and some of the drive wires 110 are anchored at the distal end of the distal section 103 to a second anchor member 109b. The drive wires 110 can be metal wires, for example, piano-type wires, stainless-steel wires, or nickel-titanium-alloy (nitinol) wires, shape memory alloy (SMA) wires, or similar structures and/or combinations thereof. The anchor members 109a and 109b have an annular shape with the center axis thereof extending along the z-axis direction similar to the guide members 108. The distal end of each drive wire 110 is fixedly coupled to one of the anchor members 109a or 109b, for example, by bonding, pinning, welding, or tightening with screws (not shown).

FIG. 2B shows perspective views of a representative guide member 108b and a representative guide member 108a. Each guide member 108 has an annular shape with the center axis Ax extending along the z-axis direction. Each guide member 108a has six wire conduits 104a, 104b, 104c, 104d, 104e, and 104f on the annular wall thereof to allow passage of corresponding six drive wires 110 there-through (one drive wire per wire conduit). Each guide member 108b has three wire conduits 104a, 104c, and 104e extending along the annular wall thereof in the lengthwise direction to allow passage for a corresponding number of drive wires 110 to pass and slide therethrough. The wire conduits 104a-104f in each guide member 108a collectively allow passage for 3 drive wires 110 which are coupled to the anchor member 109a, and 3 drive wires 110 which are coupled to the anchor member 109b. On the other hand, the wire conduits 104a, 104c, and 104e in each guide member 108b allow passage for the corresponding 3 drive wires 110 coupled to the anchor member 109b.

Exemplary movement (steering) of the steerable catheter 100 when at least some of the drive wires 110 are actively controlled to navigate the catheter through a tortuous path is described by referring to FIG. 2A and FIG. 2C. In FIG. 2A, the steerable catheter 100 having a first bending segment 103a and a second bending segment 103b is in a relaxed (compliant or non-actuated) state where no force is applied to the drive wires 110. In contrast, in FIG. 2C, the steerable catheter 100 having a single bending segment is actuated (bent) by applying a force to one or more of the drive wires 110.

In bending the steerable catheter 100, each drive wire 110 can be controlled individually by a respective actuator or motor of the actuator system 310. Alternatively, each drive wire 110 can be controlled individually by a single actuator or motor of the actuator system 310. For example, in FIG. 2C, while drive wire 110b may be fixed or anchored to the most distal anchor member 109 and to each of the guide members 108, the drive wire 110a is pulled with a control force F1, and drive wire 110c is pulled with a control force F2 (control force F2 is smaller/lower than control force F1, in this example). In this manner, the distal section 103 can be bent in a desired direction, in accordance with a combination of the driving amounts (linear displacement) of drive wires 110a and 110b. To control the posture of the catheter tip 120 of the steerable catheter 100 within two degrees of freedom, driving two drive wires (e.g., 110a and 110c) out of the three drive wires is sufficient.

In a similar manner, pulling or pushing one or more drive wires of the catheter illustrated in FIG. 1B or FIG. 2A, one or more of all bending segments can be actuated so that the postures of each bending segment may be independently controlled in accordance with the driving amounts of the individual drive wires. Further, a mechanism that actively rotates or twists the steerable catheter 100 around its central longitudinal axis Ax may be additionally provided. For example, to provide an amount of rotation or twisting to the distal end of the steerable catheter, a bending segment may be first bent in a desirable direction by driving only one drive wire, and then the body of the steerable catheter may be rotated by operating a different drive wire or by manually rotating the handle 200 relative to the axis Ax.

In FIG. 1B, FIG. 2A, FIG. 2B, and FIG. 2C each anchor member 109 and each guide member 108 have one or more wire conduits 104 and at least one tool channel 105. These components are typically constructed from Polyether Block Amide available under the tradename Pebax®. An outer sheath which covers at least part of the catheter 100 and an inner sheath (inner liner) or coating which protects the surface of tool channel 105 can also be made from Pebax. Other well known medical-grade plastics or similar composites are also viable for making components of a robotic catheter, e.g. polyurethane. Typical materials for the tubular shaft of the proximal section 102 also include polyimide and/or polyetheretherketone (PEEK), for example, which can comprise any suitable number of layers. Other materials also include thermoplastic elastomers such as, but not limited to, Pebax®, Fluorinated Ethylene Propylene (FEP); Thermoplastic Polyurethanes such as Pellethane®; silicone biomaterial such as NuSil™. These materials allow for fabrication of flexible, yet torsionally resilient steerable instruments, such as catheters and endoscopes of reduced dimensions. Similar materials as those described above can be used to manufacture the catheter tip 120 and the anti-twist housing mechanism 150.

According to one embodiment, e.g., as shown in FIG. 2A-2C, the steerable catheter 100 may have an outer diameter (OD) of about 0.14 inches, with a distal section 103 being around 2.0 inches in length, and the total length of the catheter 100 being about 24 inches. Exemplary dimensions for another prototype steerable catheter 100 are about 3.3 mm outer diameter (OD), 2.4 mm inner diameter (ID), and about 550 mm of total length. In a further exemplary embodiment, a prototype steerable catheter 100 has been designed with an inner diameter (ID) of about 0.087 to 0.089 inches (or 2.2 to 2.26 mm) at the distal end of the distal section 103. In order to provide enough clearance for suction and/or irrigation fluids in a catheter with such small diameter, the imaging device 180 (a camera) could have an OD of about 0.061 inches (1.55 mm). This means that there can be a clearance of about 0.028 inches (0.71 mm) between the inner diameter of the tool channel and the outer diameter of the camera.

Conventionally, when the distal section 103 of the catheter is actively bent and the imaging device 180 is placed inside the tool channel 105, the catheter tip 120 can twist or rotate around the camera. This is caused because the steering mechanism bends the sections of catheter attached to the driving wires, but the twisting or rotation of the catheter tip around the imaging device is a byproduct of navigation through a tortuous anatomy and friction between the anatomy and the outer surface of the catheter. To ensure that the imaging device 180 maintains its appropriate position and orientation with respect to the catheter tip 120, an anti-twist feature is disclosed herein to removably lock the imaging device 180 to the tool channel 105 at the tip of the catheter.

According to the present disclosure, it is advantageous to add anti-twist features to the catheter tip 120 to the camera, such that these anti-twist features would act as a means for mechanically interlocking the imaging device with the tip of the catheter body to avoid rotation of the camera. As used herein, interlocking of two or more components refers to mechanically locking together the two or more components for coordinating functions of the different components. To interlock two or more components refers to mechanically engaging the components with each other by overlapping or by the fitting together of mechanical features such as projections and recesses, keyways and keying tabs, keyholes and pins or keys, etc. In some embodiments, interlocking two or more components may be achieved by pressure fitting such components.

<One-Part Catheter Tip with Anti-Twist Ramp>

Figure 3A:
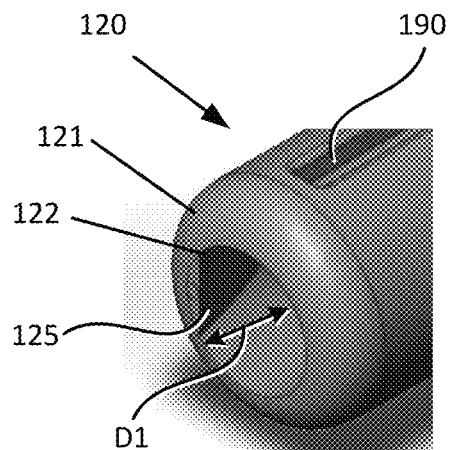
FIG. 3A, FIG. 3B, and FIG. 3C illustrates a one-part catheter tip 120 comprising a first section 120A having an inner diameter D1 where the ramp-like surface 125 is formed and a second section 120B having an inner diameter D2 (different than D1) where the ramp-like 125 is not formed, according to an embodiment of the present disclosure.
Figure 3B:
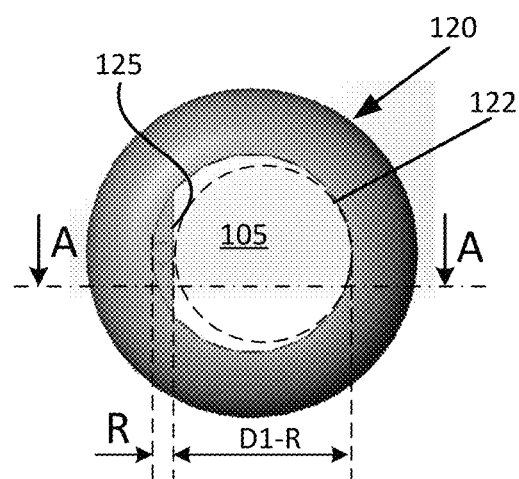
Figure 3C:
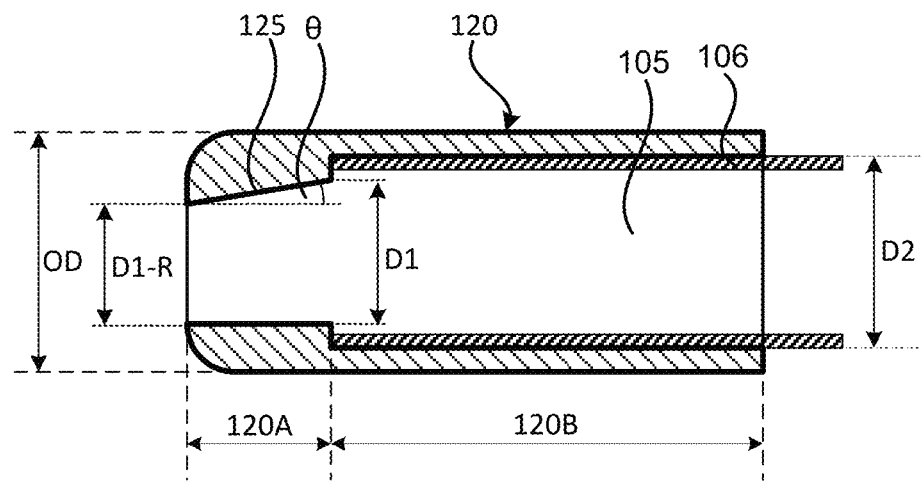

FIG. 3A, FIG. 3B, and FIG. 3C show different views of the catheter tip 120 shown in FIG. 1A-1B. According to this embodiment, the catheter tip 120 is a single-part component including anti-twist features for preventing an imaging device, such as a camera, from rotating with respect to the tool channel 105. According to one embodiment, an anti-twist feature in the shape of an inclined flat surface (ramp-like surface) is built inside the inner diameter of the catheter tip 120 of the steerable catheter 100. In one example embodiment, the entire catheter tip 120 can be made of hard plastic material by extrusion molding, or injection molding, or additive manufacture (i.e., 3D printing), or similar processes. In alternative embodiments, the catheter tip 120 can be made of separate pieces where, for example, at least an atraumatic surface 121 is made of softer polymer material or is coated with lubricious material, and the body of the catheter tip 120 is made of a single plastic tube to be pressure fitted or glued or welded to the most distal anchor member of steerable distal section 103.

It should be appreciated that adding an anti-twist feature to the tool channel 105 would potentially decrease the clearance between the imaging device and the inner diameter of the catheter body. In addition, an anti-twist feature built inside the tool channel would potentially reduce the flow rate of fluids passing through the catheter during irrigation and/or suction. Moreover, another issue to consider when adding an anti-twist feature to the tool channel 105 is the effect on flexibility and bending stability of the catheter body. To address these issues, according to one embodiment, the anti-twist feature is not provided on the steerable section but, on the catheter tip 120 attached to distal end of the steerable section. More specifically, an anti-twist feature having a ramp-like surface 125 is built-in in the catheter tip attached at the fore of the most distal bending segment. In other words, the anti-twist feature is provided on the catheter tip which does not include drive wires or conduits for drive wires. In this manner, since the catheter tip 120 does not include drive wires or conduits on its wall, the thickness of the catheter tip 120 can be used to provide the anti-twist feature without affecting flexibility or bending stability the catheter. To address the issue of reduced flow rate, an anti-twist housing mechanism 150 with a substantially rectangular outer shape complementary to the anti-twist ramp-like surface 125 is designed with a minimized footprint to provide sufficient flow rate capacity.

FIG. 3A illustrates a perspective view and FIG. 3B illustrates a front view of the catheter tip 120. As shown in FIGS. 1A through 2C, the catheter tip 120 is a tubular extension of the steerable distal section 103. The catheter tip 120 includes a rounded atraumatic surface 121 with a central opening which serves as an output port (exit port 122) for the tool channel 105. To lock the imaging device 180 to the catheter tip 120, the catheter tip 120 includes a single ramp-like surface 125 built-in inside the inner diameter of the catheter tip 120. The ramp-like surface 125 produces a simple geometry with minimal impact on the open cross sectional area of the tool channel, providing adequate flow of fluids, and the ability to pass instruments easily out the tip past the anti-twist feature. To track the position and orientation of the distal end of the catheter and/or to track an orientation of the imaging device 180, the catheter tip 120 includes an EM sensor 190 (or any other type of tracking marker or fiducial) at a known position and orientation relative to the ramp-like surface 125. For example, in FIG. 3A, the ramp-like surface 125 is positioned slightly distal to, and oriented at about 90 degrees from, the EM sensor 190. In this manner, when the imaging device 180 is inserted into the catheter tip 120, the system can easily track the position and orientation of the camera while the anti-twist feature maintains the relative position and orientation of the camera and catheter tip substantially unchanged.

FIG. 3B shows the ramp-like surface 125 can be molded into a small section (an arc) of exit port 122. More specifically, the exit port 122 is an opening with a circular cross-section with a diameter D1 approximately corresponding to the tool channel diameter. Then, the ramp-like surface 125 is formed inside diameter D1 within a portion (an arc) of the circular cross-section. For example, the ramp-like surface 125 can be molded into an arc of about 10-30 degrees of the circle defining the exit port 122. It should be noted, however, that the ramp-like surface is flat, so the surface itself is not specified to be an arc. Rather, the flat surface should extend into the inner diameter of the catheter tip enough to occupy an arc of the circle while maintaining a minimum passage through the tip to allow instruments to exit the catheter. In one embodiment, as shown in FIG. 2B, the inner diameter inside the catheter tip 120 can have a diameter D1 of about 2.2 mm; the ramp-like surface 125 is formed a distance R of about 0.2 mm inside diameter D1, so as to provide an opening or passage D1-R of about 2 mm.

FIG. 3C shows a cross-sectional view along cross-section A-A of the catheter tip 120. As shown, the catheter tip 120 can be formed as a one-part component, but it can have two distinct sections; a first section 120A where the ramp-like surface 125 is formed, and a second section 120B in which the ramp-like surface is not formed. These two sections are dimensioned so as to optimize fabrication of the ramp-like surface 125, facilitate ease of locking/unlocking the imaging device 180 to the catheter tip 120, minimize impact on the open cross-section of the tool channel 105. In one embodiment, the first section 120A can have a length of about 2 mm, and the second section 120B can have a length of about 6 mm. In addition, first section 120A has a diameter D1 (about 2.2 mm), and the second section 120B can have a larger diameter D2 (about 2.6 mm). The diameter D2 of the second section 120B allows space for an inner liner 106 (inner sheath). The inner liner 106 can be arranged in the tool channel 105 along the entire length of the steerable distal section 103, and will protrude from the most distal anchor member 109 and into the inner diameter of the distal tip 120. In this manner, the inner liner 106 facilitates insertion of the imaging device 180 to become easily aligned with the anti-twist feature (ramp-like surface 125).

The ramp-like surface is formed in a lengthwise direction staring at or near the distal end of the catheter tip 120 and tapering in a direction from the distal end towards the proximal of the catheter. More specifically, the ramp-like surface 125 is an inclined flat surface formed at an angle theta (θ) with respect to a plane parallel to the catheter axis Ax, such that the angle theta increases as the ramp-like surface 125 spans from the distal end towards the proximal end of the catheter. For example, as shown in FIG. 3B and FIG. 3C, at the distal end of the catheter tip, the ramp-like surface 125 reduces the cross-section of exit port 122 from D1 to a first dimension D1-R. Then, as the ramp-like surface 125 spans from the distal end towards the proximal end, the cross-section of tool channel 105 increases to its full diameter D1. Moreover, since the remaining section of the catheter tip does not have any conduits for drive wires, the inner diameter of the catheter tip 120 can increase to a second dimension D2 larger than the first dimension D1.

In other words, the ramp-like surface 125 is tapered/drafted in the lengthwise direction of the catheter to allow better moldability and to allow easier registration between the catheter tip 120 and the outer housing of the imaging device 180 (e.g., a flexible videoscope). The molded ramp-like surface 125 forms an anti-twist feature designed to minimally decrease the lumen size/cross sectional area of tool channel 105, while locking the position and orientation of the imaging device with respect to tool channel. When the imaging device is inserted into the catheter tip 120, the interlock feature on the imaging device will be stable enough to provide sufficient rotational stability. When the imaging device is inserted into the catheter tip 120, the ramp-like surface 125 will also facilitate unlocking of the imaging device from the catheter tip 120 without substantive force. Furthermore, when the imaging device is inserted into the catheter tip 120, the ramp-like surface 125 can prevent the imaging device from accidentally protruding (traveling) beyond the exit port 122.

From the foregoing description, in general, catheter tip 120 can have two distinct sections in the lengthwise direction; a first section 120A (distal molded section) where the ramp-like surface 125 is formed, and a second section 120B (proximal molded section) in which the ramp-like surface is not formed. The first section 120A has a length different from the length of the second section 120B (e.g., length of second section 120B is about three times the length of first section 120A). Also the first section 120A has a diameter D1 different from the diameter D2 of the second section 120B (e.g., diameter D2 is about 1.3×D1). The ramp-like surface 125 is an inclined flat surface formed inside the diameter D1 at an angle theta (θ is about 45 degrees) with respect to a plane parallel to the catheter axis Ax, such that the angle theta increases as the ramp-like surface 125 spans from the distal end towards the proximal end of the catheter.

In addition to providing a ramp-like surface 125 inside the catheter tip 120, the cross sectional area and volume of the camera housing can be minimized to optimize the flow rate of fluids. More specifically, the camera housing can be configured to have a substantially oval cross-section to minimize obstruction of the tool channel. In addition, the camera housing is provided with a flat side-surface complementary to the ramp-like surface 125 to further improve locking/unlocking of the imaging device to/from the catheter tip 120 (see FIGS. 7A and 7B).

<Two-Part Catheter Tip with Anti-Twist Ramp>

Figure 4A:
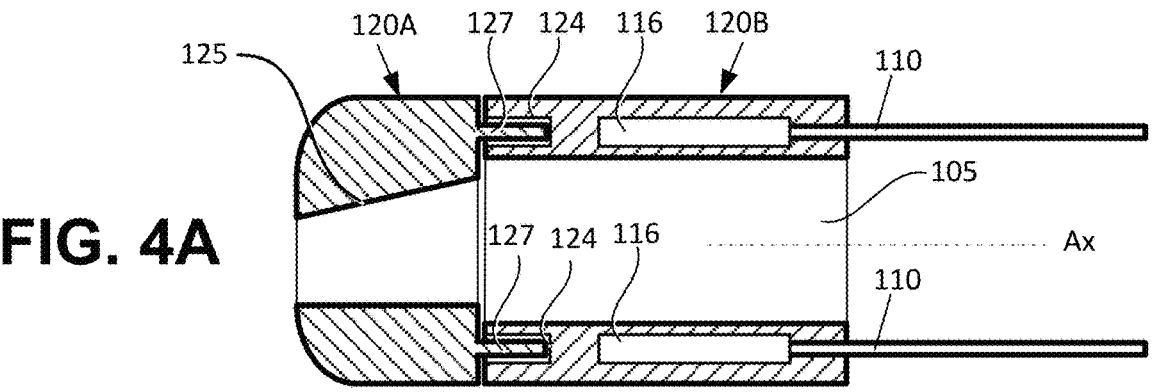
FIG. 4A, FIG. 4B, FIG. 4C and FIG. 4D illustrate various implementations of a two-part catheter tip 120 composed of two separate components including a first section 120A and a second section 120B, according to another embodiment of the present disclosure.
Figure 4B:
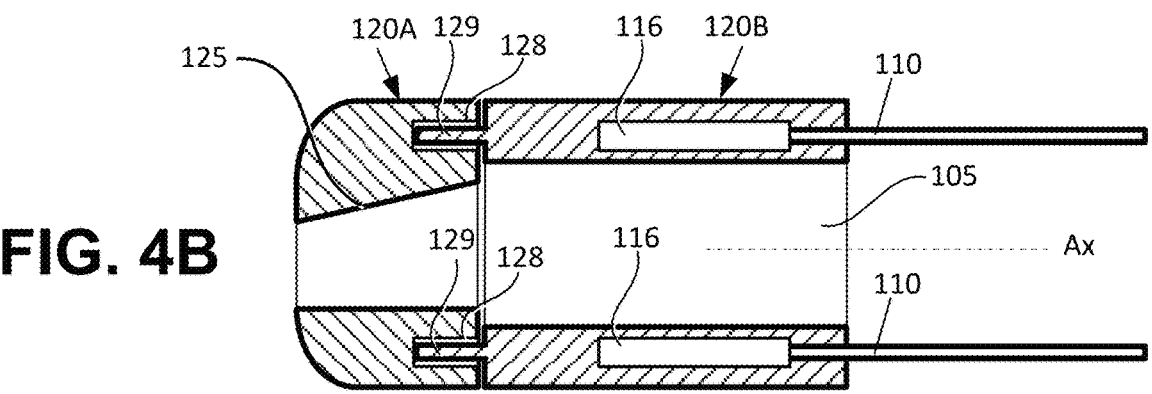

FIG. 4A through FIG. 6C illustrate an embodiment of the catheter tip 120 comprised of two separate components (a two-part catheter tip). A two-part catheter tip 120 can be implemented in several ways. FIG. 4A illustrates a two-part catheter tip 120 where the first section 120A includes pins 127 protruding from the proximal end thereof, and the second section 120B includes holes 124 at the distal end thereof to connect to the pins 127 of the first section 102A. The pins 127 are integrally formed with (are integral part of) the first section 120A. For example, the first section 102A is molded with the pins 127. The distal end of the second part 120B has anchors 116 for attaching (crimping) the drive wires 110 to the catheter tip 120. FIG. 4B illustrates a two-part catheter tip 120 where the second section 120B includes pins 129 protruding from the distal end thereof, and the first section 120A includes holes 128 at the proximal end thereof to connect to the pins 129 of the second section 120B. The pins 129 are preferably integrally formed with the second section 120B. For example, the second section 102B is molded with the pins 129 of the distal end thereof and with holes for anchors 116 on the proximal end thereof. The anchors 116 on the distal end of the second part 120B are for attaching (crimping) the drive wires 110 to the catheter tip 120, as in all embodiments of FIG. 4A-4D.

Figure 4C:
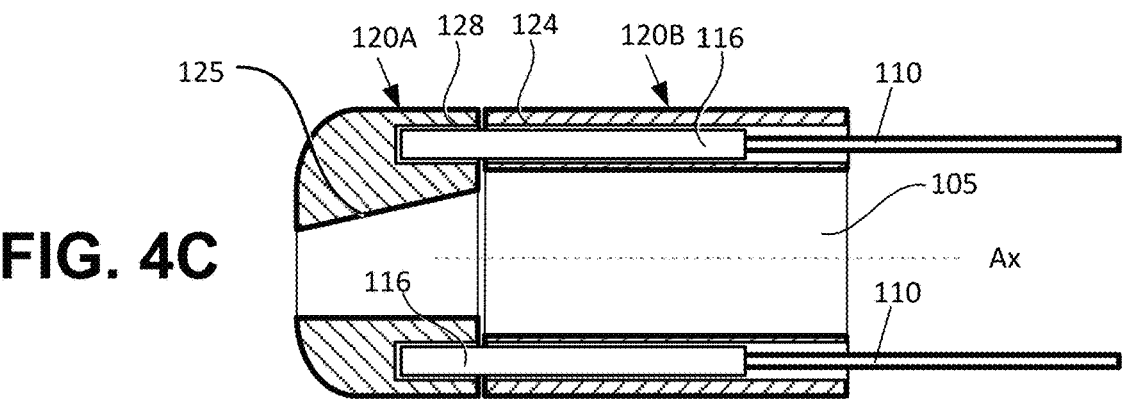

FIG. 4C illustrates a two-part catheter tip 120 where the first section 120A includes holes 128 on the proximal end thereof, and the second section 120B includes through holes 124 (conduits) spanning from the proximal end to the distal end thereof. Anchors 116 are arranged on holes 128 of the first section 120A and span onto the through holes 124 of the second section 120B. The anchors 116 are used to connect the second section 120B to the first section 120A, and also attach (crimp) the drive wires 110 to second section 120B of the catheter tip 120. In this manner, the long anchors 116 for the drive wires 110 become "pins" that connect the first section 120A to the second section 102B. According to FIG. 4B, the first section 120A can be fabricated with the ramp-like surface 125 and without protruding pins 127. The second section 120B can be fabricated with a straight cylindrical tube which is symmetric to the catheter axis Ax.

In this modified embodiment, the first section 120A can include holes 128 surrounding the inner diameter D1 of the catheter tip 120. Then, when the first section 120A is assembled with the second section 120B, the drive wires 110 can be inserted through the second section 120B and advanced into the first section 120A to be crimped by long anchors 116. In this modified embodiment, both the first section 120A and the second section 120B can be provided with through holes to pass the anchors 116 such that the drive wires 110 can be crimped to both sections (first section 120A and second section 120B) of the catheter tip 120. In this case, the first section 120A is attached to the second section 120B by a number of anchors 116 in a one to one correspondence with then number of drive wires 110.

Figure 4D:
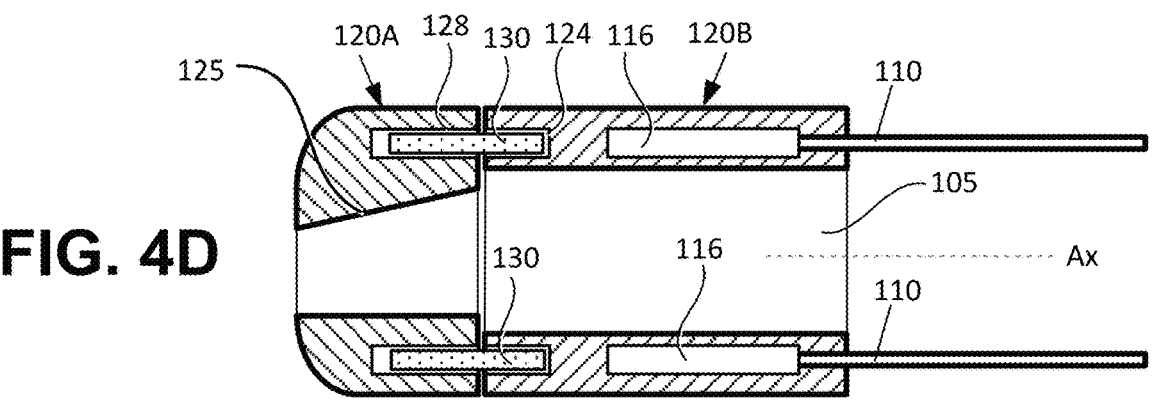

FIG. 4D illustrates a two-part catheter tip 120 where the first section 120A includes holes 128 on the proximal end thereof, and the second section 120B includes holes 124 on the distal end thereof. In this case, dedicated pins 130 are used to connect the first section 120A to the second section 120B. The holes 128 on the first section 120A and the holes 124 on the second section 120B are aligned and connected in a one to one correspondence by the dedicated pins 130. The second section 120A includes on its proximal end thereof anchors 116 to attach (crimp) the drive wires 110 to the catheter tip 120 also on a one to one correspondence. Here, it should be noted that, except for the case of FIG. 4B, the number of pins (127, 130) and the number of drive wires 110 are not necessarily equal to each other because a different number of pins can be used to attach the first section 120A to the second section 120B than the number of drive wires used to attach the catheter tip to the catheter body. In any of the embodiments of FIG. 4A-4D, the second cylindrical section 120B includes an inner liner which spans from the catheter tip to the catheter body along the tool channel, as shown in FIG. 3C. Indeed, it will be appreciated by those skilled in the art that the embodiments of distal tip 120 shown in FIG. 3C, FIG. 4A, FIG. 4B, FIG. 4C and FIG. 4D are substantially similar, and therefore these embodiments can be interchangeably combined and/or modified without undue experimentation, as long as the anti-twist feature provided by the ramp-like surface 125 and the substantially rectangular housing 150 are maintained.

Figure 5A:
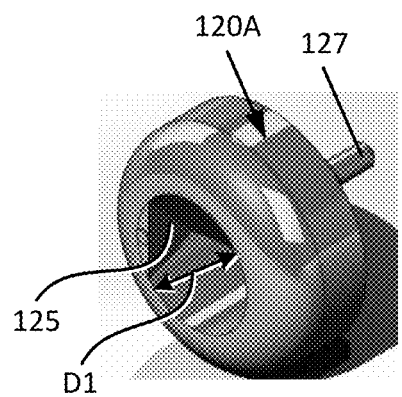
FIG. 5A, FIG. 5B and FIG. 5C shows isometric views of the two-part catheter tip 120, corresponding to the embodiment shown in FIG. 4A.
Figure 5B:
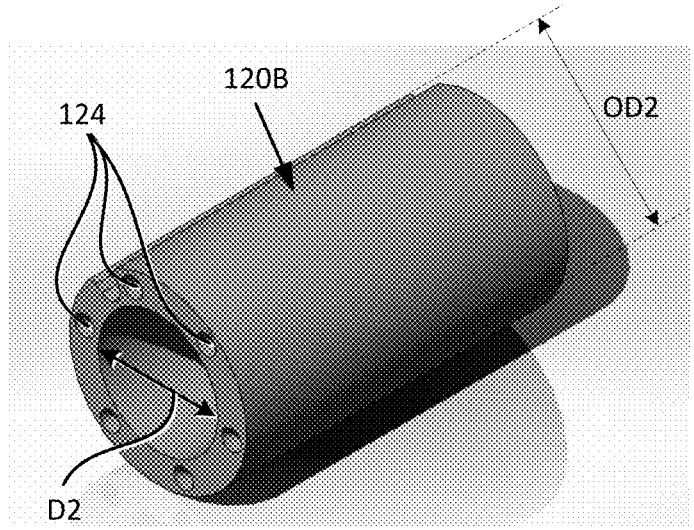
Figure 5C:
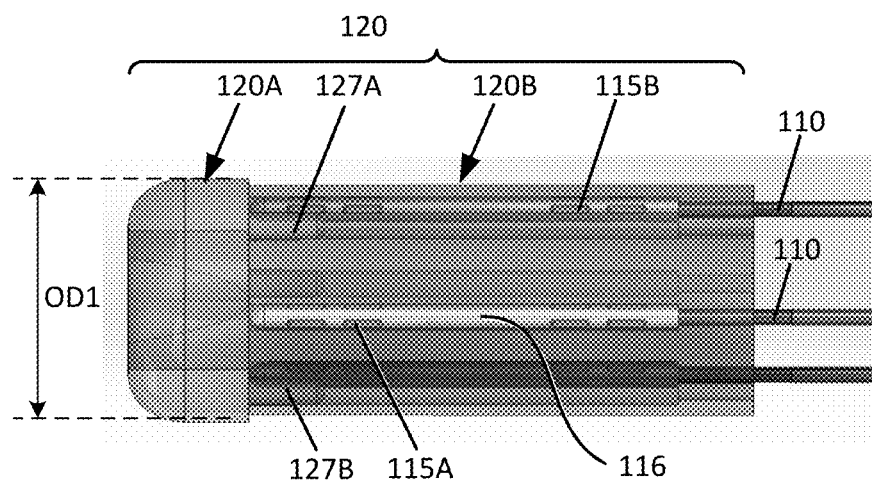

FIG. 5A, FIG. 5B and FIG. 5C shows isometric views of the two-part catheter tip 120, corresponding to the embodiment shown in FIG. 4A. FIG. 5A illustrates the first section 120A which is first cylindrical section with central opening of diameter D1 and pins 127 protruding from the proximal end thereof in a lengthwise direction. FIG. 5B illustrates the second section 120B which is a second cylindrical section with a central opening of diameter D2 and a plurality of holes 124 on the distal end along the wall of the second section 120B.

According to this embodiment, the second section 120B is a cylindrical tube formed with the central opening thereof having a diameter D2, and a plurality of holes 124 on the wall of the tube around the central opening. On the other hand, the first section 120A is formed with an atraumatic distal surface 121, a central opening of diameter D1 which serves as an exit port for the tool channel 105. The ramp-like surface 125 is formed only in the first section 120A. In this embodiment, the first section 120A includes one or more pins 127 protruding in a lengthwise direction towards the proximal end of the catheter. The holes 124, on the distal end of the second section 120B, are configured to fit therein the pins 127. Anchoring sleeves or anchors 116 are embedded in the wall of the second section 120B to secure the drive wires 110 thereto at the proximal end thereof.

FIG. 5C shows a side view of the two-part catheter tip 120 having the first section 120A assembled with the second section 120B. Assembling can be done by, for example, pressure fitting or gluing with an adhesive or welding the one or more pins 127 of the first section 102A into the holes 124 of the second section 120B. In addition, drive wires 110 can be inserted and fixed to the second section 120B. In this embodiment, the pins 127 are integrally formed with the first section 120A and can be glued with an adhesive or welded with ultrasonic or laser weld, or pressure fitted directly into the holes 124 at the distal end of the second section 120B. On the other hand, the drive wires 110 are inserted in a direction from the proximal end to the distal end of second section 120B and crimped into the to anchors 116 in one or more places along the length of the second section 120. For example, as shown in FIG. 5C, the drive wires 110 can be crimped at a first crimping point 115A very close to the first section 120A, and at a second crimping point 115B near the proximal end of the second section 120B. Those skilled in the art will appreciate that pins 127 and drive wires 110 could be inserted into separate holes 124 from different ends of the second section 120B, as shown in the FIG. 5C. Alternatively, in the holes 124 are through holes that span through the proximal end to the distal end of the second section 120B, a pin 127 can be inserted from one end and a drive wire 110 can be inserted from the opposite end into a same conduit or through hole 124 of the second section 120B to be mechanically affixed thereto.

FIG. 6A, FIG. 6B and FIG. 6C show isometric views of the two-part catheter tip 120 corresponding to the embodiment shown in FIG. 4D. FIG. 6A illustrates the first section 120A which is a first cylindrical section with a central opening of diameter D1 and through holes 128 formed on the wall of the first cylindrical section from a proximal end to the distal end thereof in a lengthwise direction. FIG. 6B illustrates the second section 120B which is a second cylindrical section with a central opening of diameter D2 and a plurality of pins 130 pressed into holes 128 formed on the distal end along the wall of the second section 120B. In this embodiment, the first section 120A has the ramp-like surface 125 as described in the previous embodiments. A notable difference in this embodiment is that the first section 120A does not include pins 127; instead, the first section 102A has holes 128 built the wall of the cylindrical section. Here, the holes 128 are either "blind" holes formed from the proximal end and not reaching the distal end of the first section 102A, or the holes 128 can be through holes formed on the wall of the tubular body spanning from the proximal end to the distal end. In this regard, the first section 120A shown in FIG. 6A applies equality to the embodiments shown in FIG. 4C and FIG. 4D. The second section 120B shown in FIG. 6B and FIG. 6C more accurately represent the embodiment shown in FIG. 4D. That is, the pins 130 pressed into the distal end of second section 120B of FIG. 6B are dedicated pins for connecting the distal molded tip to the proximal molded tip. On the other hand, in the embodiment of FIG. 4C, the anchors 116 passing through the wall of the second section 120B become the "pins" used to align and attach the first section 120A to the second section 120B of the catheter tip 120.

In other words, when the catheter tip 120 is a two-part component, the catheter tip is made of two physically separate parts. The two separate parts include a first cylindrical section (first section 102A) and a second cylindrical section (second section 120B) arranged in a direction from the distal end towards the proximal end. In all implementations of the two-part catheter tip 120, the first cylindrical section has a ramp-like surface 125 in the inner diameter thereof, and second cylindrical section has a hollow inner core and conduits on the wall thereof for a plurality of drive wires attached at the proximal end thereof. In a first implementation, the first cylindrical section has integrally formed pins 127 protruding from the proximal end thereof. In a second, third and fourth implementation, the first cylindrical section has holes 124 formed along the wall from the proximal end toward the distal end thereof. The holes 124 can be "blind" holes formed only at the proximal end of the first cylindrical section, or can be through holes (conduits) spanning from the proximal end to the distal end of the first cylindrical section. In the first implementation, the second cylindrical section includes holes 124 at the distal end thereof to connect with the pins 127 of the first cylindrical section. In the second implementation, the second cylindrical section includes integral pins 129 protruding from the distal end thereof to connect with the holes 128 of the first cylindrical section.

In the third implementation, the second cylindrical section has through holes 124 formed along the wall spanning from the proximal end to the distal end. Long anchors 116, which function as "pins" to connect the first section 120A to the second section 120B, are arranged in the holes 128 of the first cylindrical section and the holes 124 of the second cylindrical section. In the fourth implementation, the second cylindrical section includes holes 124 at the distal end thereof to connect with the dedicated pins 130 which connect the first cylindrical section to the second cylindrical section. In this implementation, the dedicated pins 130 are fabricated separately from the first section 120A and the second section 120B. Advantageously, the dedicated pins 130 can be made of radiopaque material and used for determining position of the distal tip 120.

Having the catheter tip 120 made of two separate parts, where the first section 120A becomes the most distal anchor for the drive wires reduces the overall rigid length of the catheter tip 120. In one embodiment, the rigid length of the catheter tip 120 can be reduced by as much as 2.0 mm as compared to the embodiment where the catheter tip 120 is a one-part component and the drive wires are not attached to the catheter tip 120. Here, it is noted that the two-part construction of the catheter tip is not necessarily the only reason why a reduction in rigid length is achieved. A reduction of rigid length of the catheter tip is achieved due to the fact that the actuation wires are embedded in the proximal section of the molded catheter tip as opposed to having a molded tip and a separate distal anchor for the drive wires. Therefore, if the drive wires were to be attached directly to the proximal section of the one-part catheter tip 120, at least some reduction of rigid length could also be achieved in such embodiment.

The two-part catheter tip 120 can also improve the navigation capability of the catheter. Separating the catheter tip 120 into two parts allows through holes to be formed in the first cylindrical section and/or the second cylindrical section so no windows are needed to support the core pins during molding. Specifically, in a molding process for making a molded part, if blind holes are to be added into the molded part, that means there will be core pins floating in the cavity without any support. The floating pins may deflect during injection, so the end of the core has to be supported. These supports require metal features in the mold that create openings in the molded part, i.e. windows. In contrast, when the distal tip is formed by two separate parts, each part can be molded separately so no openings (windows) are created during the molding process.

Having the catheter tip made of two parts also makes it easier (allows more access) to attach the first section 120A to an inner liner 106, as shown in FIG. 3C. Specifically, referring back to FIG. 3C, an inner liner 106 is arranged through the inner diameter of the steerable distal section 103 and through the second section 120B of the catheter tip 120. When the catheter tip 120 is made of two separate parts, the inner liner 106 can be extended to the first section 120A.

Making the second section 120B the most distal anchor allows the use of a longer tube anchor 116 with sufficient space for multiple full (double) crimps for attaching the drive wires 110 to the catheter tip. For example, each drive wire can be attached with a first crimp 115A and a second crimp 115B, as shown in FIG. 5C. Attaching the drive wires with double crimps to the second section 120B can produce a catheter tip more resilient to torsional effects. For example, double crimp can provide a 50+N tensile strength of the anchor to the wire. Incidentally, the modified two-part catheter tip shown in FIG. 4D can provide even more tensile strength when the drive wires are crimped to the first section 120A and to the section 120B.

With a single part catheter tip, the molded tip gets placed onto the end of the inner liner 106 (as shown in FIG. 3C), which has to be cut to a precise length to fit within the counterbore of the tip. Then, for gluing purposes, it is possible to only dispense glue on the proximal side of the tip (right). In contrast, with the two part catheter tip, it is possible to place the second section 102B onto the inner liner and apply glue on both sides, and then trim the inner liner flush to the molded part. Afterwards, the first section 120A of the tip can be attached to the second section 120B that has been glued to the inner liner. Accordingly, while the two-part catheter tip may need additional assembling steps (as compared to the one-part catheter tip), the two-part embodiment can provide higher tensile strength and reduced rigid length of the catheter tip 120.

An additional advantage of the two-part catheter tip 120 is that it is possible to dimension the outer diameter of the second section 120 to fit an outer liner (not shown) to protect the catheter body. In FIG. 5C and FIG. 6C, for example, the outer diameter (OD1) of the first section 120A is slightly larger than the outer diameter (OD2) of the second section 120B. This difference in outer diameters OD1>OD2, forms a small space around the second section 120B where an outer liner or outer sheath will be arranged and secured.

<Anti-Twist Housing Mechanism>

Figure 7A:
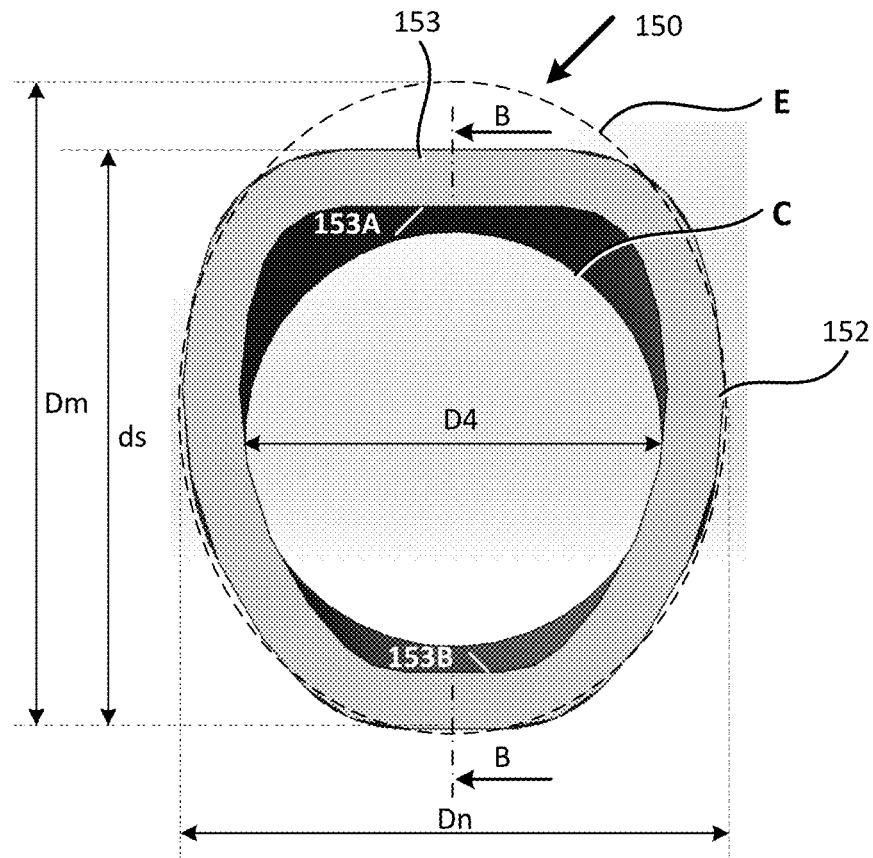
FIGS. 7A and 7B show an anti-twist housing mechanism 150 configured to be attached to an endoscope camera (imaging device 180) and inserted through the tool channel 105 so that the housing mechanism 150, with the imaging device 180 therein, becomes interlocked with the catheter tip 120 to prevent rotation of the housing mechanism 150 and imaging device 180 with respect to the tool channel and/or prevent twisting of the catheter tip 120 with respect to the housing mechanism 150 and the imaging device 180.
Figure 7B:
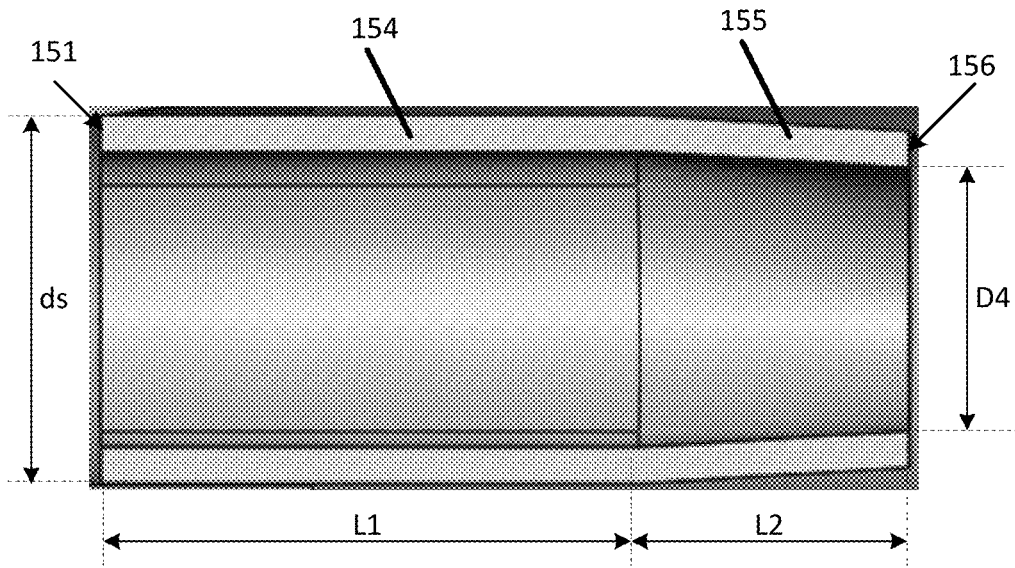

FIG. 7A and FIG. 7B show an anti-twist housing mechanism 150 configured to be attached to an endoscope camera (imaging device 180), and inserted through the tool channel 105 to be locked with the catheter tip 120. The anti-twist housing mechanism 150 is advantageously shaped into a substantially rectangular body having at least one surface complementary to the ramp-like surface 125 built into the opening of the catheter tip 120. FIG. 7A shows a front view and FIG. 7b shows a cross-sectional view along cross-section B-B of the anti-twist housing mechanism 150. As shown in FIG. 7A and FIG. 7B, the anti-twist housing mechanism 150 is a casing or chassis structure configured to fit into the tool channel 105 and advanced through the catheter body to the catheter tip 120. Once the anti-twist housing mechanism 150 is inserted into the catheter tip 120, the housing mechanism 150 will hold the imaging device 180 in a predetermined orientation without allowing rotation of the imaging device.

The anti-twist housing mechanism 150 is a tubular member configured to enclose and hold the imaging device 180 in a predetermined orientation. The housing mechanism 150 is formed of a first tubular section 154 and a second tubular section 155 contained in the lengthwise direction between a distal end 151 and a proximal end 156 with a hollow space therebetween (as shown in FIG. 7B). The first tubular section 154 has a length L1 different from a length L2 of the second tubular section 155. In one embodiment, length L1 is about 3.5 mm, while length L2 is about 1.5 mm. In other words, the length of the first tubular section 154 is about 2.33 times the length of the second tubular section 155. In addition, a cross-sectional dimension (e.g., diameter) of the first tubular section 154 is different from that of the second tubular section 155.

The cross-section of the distal end 151 is substantially rectangular having at least one flat side-surface 153 and one or more than one curved surface 152 (see FIG. 7A). The curved surface 152 is defined by an ellipse E having a minor diameter Dn and a major diameter Dm. In one embodiment, minor diameter Dn is about 1.8 mm and the major diameter Dm is about 2.5 mm. The major diameter Dm is substantially equal to the diameter D2 of the tool channel 105 (inner diameter of the catheter 100). The flat side-surface 153 is formed in the lengthwise direction along a plane parallel to the catheter axis Ax, such that the flat surface 153 is perpendicular to the direction of the major diameter Dm. In other words, the first cylindrical section 154 fits within a substantially elliptical cylinder with one flat side-surface 153 extending in the lengthwise direction along the narrow side of the elliptic cylinder.

The cross-section of the proximal surface 156 is defined by a continuous curved surface that fits into a circle C which has a diameter D4. In one embodiment, the circle C has a diameter D4 of about 1.6 mm. In other words, the second cylindrical section 154 is a conical cylinder spanning from one end of the first cylindrical section (elliptic cylinder) and ending in the proximal surface 156 which fits into circle C of diameter D4. The diameter D4 can be substantially smaller than the inner diameter of the tool channel 105 to allow sufficient flow rate of fluids during a procedure. For example, in one embodiment, the tool channel 105 can have diameter of about 2.5 mm while the diameter of the anti-twist housing mechanism at the proximal end thereof is about 1.5 mm.

The anti-twist housing mechanism 150 is a generally rectangular housing with at least one flat side-surface extending in the lengthwise direction of the tool channel. At the distal end 151, the substantially rectangular housing fits within an ellipse E, and at the proximal end 156, the substantially rectangular housing fits within a circle C. In at least one embodiment, at the distal end 151, the anti-twist housing mechanism 150 can have an elliptical (curved) surface 152 and more than one flat side-surface. For example, in FIG. 7A, the flat side side-surface 153 can include a first flat surface 153A (upper part of FIG. 7A), and a second flat surface 153B (lower part of FIG. 7A). A dimension "ds" of the substantially rectangular housing taken in a direction along the major axis of the ellipse is defined from one end (vertex) to approximately a focus on the other side of the vertex. In one example, the distance ds is about 1.5 mm to 1.6 mm.

At the proximal end 156, the anti-twist housing mechanism 150 has a circular or oval cross-section such that the outer surface of the second tubular section 155 fits into a circle C of diameter D4. It can be appreciated, therefore, that anti-twist housing mechanism 150 can have a substantially rectangular shape with at least one flat side-surface 153, wherein the at least one flat side-surface 153 is configured to lock the outer surface of the housing mechanism 150 with the ramp-like surface 125 of the catheter tip 120. Moreover, the at least one flat side-surface 153 is configured to lock the inner surface of the housing mechanism 150 with the imaging device 180.

The anti-twist housing mechanism 150 disclosed herein can be made of a thin metal sheet, and/or thin metal tubes (e.g., hypotubes), or can be molded plastic extrusion reinforce with thin wires or fibers. The material thickness of the anti-twist housing mechanism 150 should be relatively low (thin), so that the housing mechanism will only minimally reduce the cross sectional area of the tool channel and thus optimize fluid flow. However, if the material thickness is excessively low (too thin), the anti-twist housing mechanism 150 could deflect or bend, allowing some twisting to occur. Therefore, those skilled in the art will strive to find a balance between increasing the material thickness to reduce the possibility of bending or collapsing, and decreasing the material thickness to optimize fluid flow.

Figure 8A:
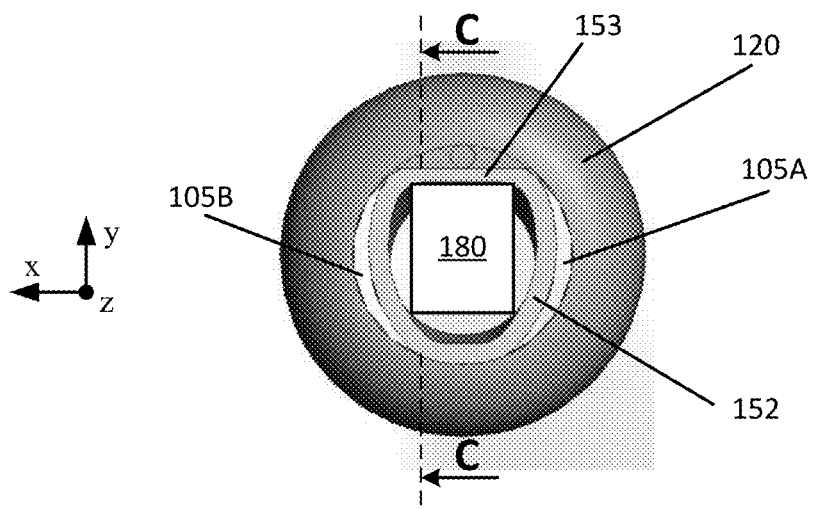
FIG. 8A shows a front view and FIG. 8B a cross-sectional view of the anti-twist housing mechanism 150 inserted into the catheter tip 120, wherein the housing mechanism 150 has a substantially rectangular cross-section with a flat surface 153 which is interlocked with the catheter tip 120 by the ramp-like surface 125 to prevent rotation of an imaging device 180 with respect to the tool channel and/or prevent twisting of the catheter tip 120 with respect to the imaging device 180.
Figure 8B:
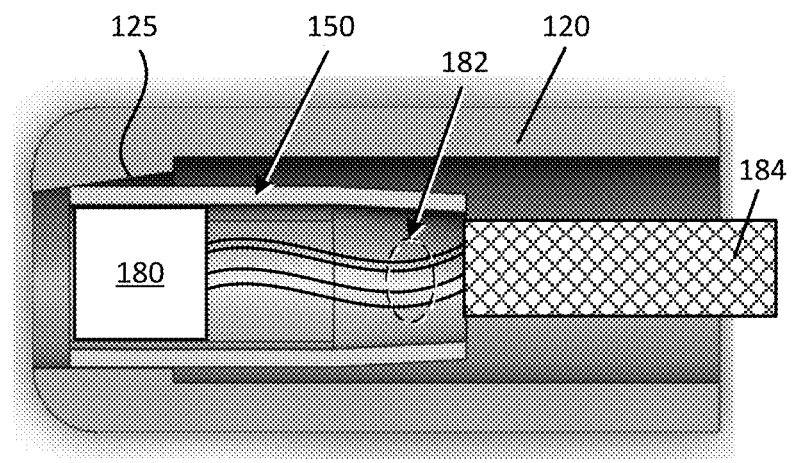

FIG. 8A and FIG. 8B show a front view and a cross-sectional view along cross-section C-C of the anti-twist housing mechanism 150 inserted into the catheter tip 120. The anti-twist housing mechanism 150 is configured to maintain an imaging device 180 at predetermined orientation with respect to the catheter tip 120. As shown in FIG. 8A, the imaging device 180 can be mounted in the anti-twist housing mechanism 150 with a predetermined orientation where, for example, the y-axis is aligned with the direction of gravity, the z-axis is aligned with the catheter axis Ax, and the x-axis is aligned with a side of the imaging device 180. In at least one embodiment, the imaging device 180 may include a miniature CMOS sensor or a CCD camera along with electronic control boards and illumination optics such as light emitting diodes and/or optical fibers.

The anti-twist housing mechanism 150 includes the at least one flat side-surface 153 to fit (receive) a rectangular shape of the camera, and the anti twist features (ramp-like surface 125) in the catheter tip will keep the orientation of the camera and catheter tip more consistent. Therefore, when the anti-twist housing mechanism 150 is inserted into the catheter tip 120, will allow more intuitive navigation since the orientation of the camera FOV will better correspond to navigation inputs of the controller, i.e., right command will correspond to right movement and display, and up command will correspond to an up, movement and display, etc., throughout the procedure. The small footprint of the anti-twist features will also allow sufficient flow of fluids (e.g., suction and irrigation) to be performed without having to remove the camera.

FIG. 8B illustrates a cross-sectional view of the camera 180 held within the housing portion of the anti-twist housing mechanism 150 and interlocked by the ramp-like surface 125 to the tool channel at catheter tip 120. As shown in FIG. 8A, the anti-twist housing mechanism 150, i.e., housing mechanism or substantially rectangular housing, includes the flat side-surface 153 and the curved surface 152. The curved surface 152 fits into an ellipse E. The minor diameter Dn of the ellipse E is dimensioned so that the outer surface of the housing mechanism 150 is smaller than the inner diameter of the tool channel 105; this allows a clearance 105A and 105B between the tool channel 105 and the housing mechanism 150. This clearance 105A and 105B will ensure that the tool channel 105 maintains sufficient flow for irrigation and/or suction of fluids during certain procedures without removing the housing mechanism 150 and/or the imaging device 180.

Referring back to FIG. 1B and FIG. 3A, the catheter tip 120 may include one or more than one electromagnetic (EM) sensors 190 arranged at a predetermined position and/or orientation with respect to the ramp-like surface 125. A tracking system such as an EM tracking system (not shown), can track the position and/or orientation of the catheter tip 120 and/or the imaging device 180 (camera). Active tracking can be implemented by, for example, intraoperative imaging, as described in U.S. Pat. No. 6,380,732, which is incorporated by reference herein for all purposes.

As shown in FIG. 8B, the anti-twist housing mechanism 150 may enclose the imaging device 180 together with other components such as optical fibers and/or electrical cables 182. These cables 182 can be used to electrically connect the camera and/or the EM sensors 190 to electronic circuitry located outside (e.g., in the handle) of the steerable catheter 100. In addition, optical fibers may be used for illumination of the lumen 80 when imaging with the camera. Therefore, a flexible cable bundle 184 may be attached to the housing mechanism 150; the cable bundle 184 can enclose the optical fibers and/or electrical cables 182 strung together and passed through the tool channel 105. Since the camera 180 is powered by delicate electrical cables 182, and may also include delicate optical fibers (e.g., for illumination), rotation of the camera inside of the tool channel is highly undesirable. However, in order to easily swap a flexible videoscope for one or more end-effector tools, it is advantageous that the camera can be quickly deployed and withdrawn through the tool channel 105 by a linear movement along the catheter axis Ax. In this regard, the ramp-like surface 125 cooperates with the anti-twist housing mechanism 150 having a flat side-surface 152 to facilitate quick deployment and withdrawal of the imaging device 180 while maintaining appropriate image orientation and sufficient fluid flow rate.

According to the various embodiments, since the ramp-like surface 125 easily engages with the flat side-surface 153 of the anti-twist housing mechanism 150, and provides enough force to prevent rotation of the imaging device 180 (a camera or videoscope) with respect to the tool channel. The anti-twist features (ramp-like surface 125 and anti-twist housing mechanism 150) not only maintain the camera's position and orientation substantially unchanged, but also protect the electrical and/or optical connections of the imaging device from becoming damaged and/or disconnected. In addition, the anti-twist housing mechanism 150 reinforces the catheter tip 120. Furthermore, the tapered molded features of the ramp-like surface 125 will allow easier registration between the catheter tip 120 and the videoscope camera.

The MCR has a removable camera that interlocks with the catheter tip via anti-twist features without increasing the overall profile of the catheter body. The anti-twist features will keep the orientation of the camera with respect to the catheter tip more consistent, and thus allow more intuitive navigation since the camera field-of-view will better correspond to navigation inputs, i.e., a right control input will correspond to right movement, and up control input will correspond to upright movement, etc. throughout the procedure. The features will also still allow suction and irrigation to be performed without having to remove the camera. This feature is also important because, during image guidance, the gap between the camera and the catheter inner wall is also used to supply/remove fluids (e.g., water or gas) to clean bodily substances (e.g., mucus) blocking the camera view.

The various embodiments of anti-twist features disclosed herein are described as applicable to a Medical Continuum Robotic (MCR) catheter system including a flexible videoscope. However, the present disclosure is not limited thereto. Any endoscope system that needs to maintain the endoscope image substantially unchanged can implement and benefit from the anti-twist features disclosed herein.

Some considerations for optimizing the advantageous effects of the anti-twist feature disclosed herein include: The distal tip of the catheter will incorporate features that can be molded into it, and will act as an interlock between the catheter tip 120 and the anti-twist housing mechanism of flexible videoscope; the molded features of the ramp-like surface will easily engage with the anti-twist housing to interlock the distal tip with the videoscope; the molded features can be tapered/drafted to allow easier registration (coupling) between the tip and the videoscope; the molded features are designed to minimally decrease lumen size/ cross sectional area of the tool channel; the anti-twist feature can be permanently attached to the distal end of the videoscope; the anti-twist feature on the videoscope will be stable enough to provide sufficient rotational stability to maintain image orientation substantially unchanged; the cross sectional area and overall volume of the anti-twist feature are minimized to optimize fluid flow without removing the videoscope imaging device.

The present disclosure is not limited to the foregoing considerations, features, and advantages. Several aspects, specifically twenty five aspects, of the present disclosure are set forth in the Listing of Claims numbered 1-25. Additional aspects include, but are not limited to the following:

Aspect 26: A steerable catheter configured to be actuated by an actuator unit via one or more drive wires, the steerable catheter comprising: a catheter body having a tool channel which spans from a proximal end to a distal end of the catheter body along a catheter axis; and a catheter tip attached to the distal end of the catheter body and configured to mate with a substantially rectangular housing of an imaging device inserted through the tool channel, wherein the tool channel has a tool channel diameter centered about the catheter axis and the catheter tip has an opening aligned with the tool channel in a lengthwise direction along the catheter axis, and wherein the catheter tip includes a ramp-like surface formed inside the opening at an angle with respect to a plane parallel to the catheter axis such that the angle increases as the ramp-like surface spans from the distal end towards the proximal end of the catheter tip.

Aspect 27. The steerable catheter according to aspect 26, wherein, in order from the distal end to the proximal end, the catheter tip includes a first cylindrical section and a second cylindrical section, and wherein the first cylindrical section has an inner diameter and an outer diameter, and the second cylindrical section has an inner diameter and an outer diameter.

Aspect 28. The steerable catheter according to aspect 27, wherein the inner diameter of the first cylindrical section has a dimension different from that of the inner diameter of the second cylindrical section, and wherein the outer diameter of the first cylindrical section has a dimension different from that of the outer diameter of the second cylindrical section.

Aspect 29. The steerable catheter according to aspect 29, further comprising: an inner liner arranged against the inner diameter of the second cylindrical section and spanning through the tool channel diameter towards the proximal end of the catheter body; and an outer liner arranged against the outer diameter of the second cylindrical section and spanning through an outer surface of the catheter body towards the proximal end of the catheter body.

Aspect 30. The steerable catheter according to aspect 26, wherein the first cylindrical section and the second cylindrical section are manufactured as a one-part component.

Aspect 31. The steerable catheter according to aspect 26, wherein the first cylindrical section and the second cylindrical section are manufactured as a two-part component.

Aspect 32. The steerable catheter according to aspect 31, wherein the first cylindrical section includes a plurality of pins integrally formed at a proximal end thereof, and the second cylindrical section includes a plurality of holes at a distal end thereof and a plurality of anchors inserted along a wall of the second cylindrical section in a direction from a proximal end to a distal end thereof, wherein the plurality of holes on the distal end of the second cylindrical section are configured to connect to the plurality of pins of the first cylindrical section in a one to one correspondence, and wherein the plurality of anchors in the second cylindrical section are configured to connect to the one or more drive wires of the steerable catheter. [FIG. 4A]

Aspect 33. The steerable catheter according to aspect 31, wherein the first cylindrical section includes a plurality of holes formed in a direction from a proximal end to a distal end thereof, and the second cylindrical section includes a plurality of pins integrally formed at a distal end thereof and protruding towards the first cylindrical section, a plurality of anchors inserted along a wall of the second cylindrical section in a direction from a proximal end to a distal end thereof, wherein the plurality of holes on the proximal end of the first cylindrical section are configured to connect to the plurality of pins of the second cylindrical section in a one to one correspondence, and wherein the plurality of anchors in the second cylindrical section are configured to connect to the one or more drive wires of the steerable catheter. [FIG. 4B]

Aspect 34. The steerable catheter according to aspect 31, wherein the first cylindrical section includes a plurality of holes formed in a direction from a proximal end to a distal end thereof, and the second cylindrical section includes a plurality of through holes formed along a wall of the second cylindrical section spanning from a distal end to a proximal end thereof, wherein a plurality of anchors are inserted along the through holes of the second cylindrical section and into the plurality of holes of first cylindrical section in a one to one correspondence, such that the first cylindrical section becomes connected to the second cylindrical section by the plurality of anchors, and wherein, at the proximal end of the second cylindrical section, the plurality of anchors are configured to connect to the one or more drive wires of the steerable catheter in a one to one correspondence. [FIG. 4C]

Aspect 35. The steerable catheter according to aspect 31, further comprising: a plurality of dedicated pins configured to align and connect the first cylindrical section to the second cylindrical section, wherein the first cylindrical section includes a plurality of holes formed in a direction from a proximal end to a distal end thereof, and the second cylindrical section includes a plurality of holes formed in a direction from a distal end to a proximal end thereof, wherein the plurality of holes on the proximal end of the first cylindrical section and the plurality of holes on the distal end of the second cylindrical section are configured to connect to the plurality of dedicated pins in a one to one correspondence, and wherein the plurality of anchors in the second cylindrical section are configured to connect to the one or more drive wires of the steerable catheter. [FIG. 4D]

<Software Related Disclosure>

At least certain aspects of the exemplary embodiments described herein can be realized by a computer system or apparatus that reads out and executes computer executable instructions (e.g., one or more programs or executable code) recorded on a storage medium (which may also be referred to as a 'non-transitory computer-readable storage medium') to perform functions of one or more block diagrams or flowchart diagrams described above. The computer may include various components known to a person having ordinary skill in the art. For example, the computer system 400 may include a signal processor implemented by one or more circuits (e.g., a field programmable gate array (FPGA) or an application specific integrated circuit (ASIC)) for performing the functions of one or more of the above-described embodiment(s), by, for example, reading out and executing the computer executable instructions from the storage medium to perform the functions of one or more of the above-described embodiment(s) and/or controlling the one or more circuits to perform the functions of one or more of the above-described embodiment(s). The computer system 400 may comprise one or more processors (e.g., central processing unit (CPU) 410, micro processing unit (MPU)), and may include a network of separate computers or separate processors to read out and execute the computer executable instructions. The computer executable instructions may be provided to the computer, for example, from a cloud-based network or from the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like. The computer may include an input/output (I/O) interface to receive and/or send communication signals (data) to input and output devices, which may include a keyboard, a display, a mouse, a touch screen, touchless interface (e.g., a gesture recognition device) a printing device, a light pen, an optical storage device, a scanner, a microphone, a camera, a drive, communication cable and a network (either wired or wireless).

Modifications and/or Combinations of Embodiments

In referring to the description, specific details are set forth in order to provide a thorough understanding of the examples disclosed. In other instances, well-known methods, procedures, components and circuits have not been described in detail as not to unnecessarily lengthen the present disclosure. Unless defined otherwise herein, all technical and scientific terms used herein have the same meaning as commonly understood by persons of ordinary skill in the art to which this disclosure belongs. In that regard, breadth and scope of the present disclosure is not limited by the specification or drawings, but rather only by the plain meaning of the claim terms employed.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. All embodiments can be modified and/or combined to improve and or simplify the anti-twist feature as applicable to specific applications. The scope of the following claims is to be accorded the broadest interpretation so as to encompass all such modifications and equivalent structures and functions.

Any patent, pre-grant patent publication, or other disclosure, in whole or in part, that is said to be incorporated by reference herein is incorporated only to the extent that the incorporated materials do not conflict with standard definitions or terms, or with statements and descriptions set forth in the present disclosure. As such, and to the extent necessary, the disclosure as explicitly set forth herein supersedes any conflicting material incorporated by reference.

What is claimed is:

1. A steerable catheter configured to be actuated by an actuator unit, the steerable catheter comprising:
    a catheter body having a catheter tip and a tool channel configured to receive a substantially rectangular housing therein, wherein the catheter tip includes a ramp-like surface formed in at least part of the tool channel, wherein the substantially rectangular housing includes a side-surface configured to engage with the ramp-like surface of the catheter tip to prevent rotation of the substantially rectangular housing with respect to the tool channel and/or prevent twisting of the catheter tip with respect to an imaging device within the substantially rectangular housing, and wherein, when inserted into the catheter tip, a clearance is formed between the tool channel and the substantially rectangular housing to allow an unobstructed flow of fluids through the tool channel without removing the substantially rectangular housing and/or the imaging device from the catheter tip.

2. The steerable catheter according to claim 1, further comprising:

wherein the imaging device is configured to detachably attach inside the substantially rectangular housing at or near a distal end of the catheter tip.

3. The steerable catheter according to claim 2, wherein the catheter tip includes a first cylindrical section and a second cylindrical section that are manufactured as a single part component.

4. The steerable catheter according to claim 3, wherein the first cylindrical section serves as an exit port for the tool channel, and the exit port includes an atraumatic surface at the distal end of the catheter tip, wherein the second cylindrical section includes an inner liner which spans from the catheter tip to the catheter body along the tool channel, and wherein the ramp-like surface is configured to removably mate in a lengthwise direction with the side-surface of the substantially rectangular housing.

5. The steerable catheter according to claim 2, wherein the first cylindrical section and the second cylindrical section of the catheter tip are manufactured as a two-part component.

6. The steerable catheter according to claim 5, wherein the tool channel spans along a catheter axis from a proximal end of the catheter body to the catheter tip, and wherein the first cylindrical section includes the ramp-like surface which is asymmetric with respect to the catheter axis, and the second cylindrical section includes a straight cylindrical surface which is symmetric with respect to the catheter axis.

7. The steerable catheter according to claim 5, wherein the first cylindrical section includes an atraumatic surface at a distal end thereof and one or more pins integrally formed with the first cylindrical section and protruding from a proximal end thereof, and wherein the second cylindrical section includes a plurality of conduits spanning through a wall of the second cylindrical section from a proximal end to a distal end thereof.

8. The steerable catheter according to claim 7, wherein the plurality of conduits on the distal end of the second cylindrical section are configured to connect to the one or more pins of the first cylindrical section in a one to one correspondence.

9. The steerable catheter according to claim 7, wherein the actuator unit actuates the steerable catheter via one or more drive wires, and wherein the plurality of conduits on the proximal end of the second cylindrical section are configured to connect to the one or more drive wires of the steerable catheter on a one to one correspondence.

10. The steerable catheter according to claim 5, wherein the first cylindrical section of the catheter tip includes an atraumatic surface at a distal end thereof and a plurality of conduits on a proximal end thereof, and wherein the second cylindrical section of the catheter tip includes a plurality of conduits spanning lengthwise along a wall thereof from a proximal end to a distal end of the second cylindrical section.

11. The steerable catheter according to claim 10, wherein the plurality of conduits of the second cylindrical section include a plurality of anchors protruding from the distal end of the second cylindrical section and extending towards the first cylindrical section, and wherein the plurality of conduits on the proximal end of the first cylindrical section are configured to connect with the plurality of anchors protruding from the second cylindrical section in a one to one correspondence.

12. The steerable catheter according to claim 10, wherein the actuator unit actuates the steerable catheter via one or more drive wires, and wherein the plurality of anchors included in the plurality of conduits of the second cylindrical section are configured to attach at the proximal end thereof to the one or more drive wires of the steerable catheter in a one to one correspondence.

13. The steerable catheter according to claim 5, wherein the first cylindrical section of the catheter tip includes an atraumatic surface at a distal end thereof and a plurality of conduits on a proximal end thereof, and wherein the second cylindrical section of the catheter tip includes a plurality of conduits on the distal end thereof and a plurality of anchors along a wall thereof near a proximal end of the second cylindrical section.

14. The steerable catheter according to claim 13, further comprising a plurality of dedicated pins configured to align and connect the first cylindrical section to the second cylindrical section, wherein the plurality of dedicated pins are inserted into the plurality of conduits on the distal end of the second cylindrical section and in the plurality of conduits on the proximal end of the first cylindrical section in a one to one correspondence.

15. The steerable catheter according to claim 13, wherein the actuator unit actuates the steerable catheter via one or more drive wires, and wherein the plurality of anchors near the proximal end of the second cylindrical section are configured to connect to the one or more drive wires of the steerable catheter.

16. The steerable catheter according to claim 5, wherein the first cylindrical section of the catheter tip includes an atraumatic surface at a distal end thereof and a plurality of conduits on a proximal end thereof, and wherein the second cylindrical section of the catheter tip includes a plurality of pins protruding from the distal end thereof and a plurality of anchors along a wall thereof near a proximal end of the second cylindrical section.

17. The steerable catheter according to claim 16, wherein the plurality of pins protruding from the distal end of the second cylindrical section are inserted into the plurality of conduits on the proximal end of the first cylindrical section in a one to one correspondence.

18. The steerable catheter according to claim 16,
wherein the actuator unit actuates the steerable catheter via one or more drive wires, and
wherein the plurality of anchors near the proximal end of the second cylindrical section are configured to connect to the one or more drive wires of the steerable catheter.

19. The steerable catheter according to claim 1,
wherein the substantially rectangular housing is insertable into and removable from the catheter tip through the tool channel together with the imaging device.

20. The steerable catheter according to claim 1,
wherein the ramp-like surface reduces a cross-section of the tool channel at the distal end of the catheter tip, and thereby prevents the substantially rectangular housing and/or the imaging device from traveling distally beyond the first section of the catheter tip.

21. The steerable catheter according to claim 1,
wherein the substantially rectangular housing includes with at least one flat side-surface and a curved surface spanning lengthwise from a distal end to a proximal end of the catheter tip; and
wherein the imaging device is permanently attached to the housing mechanism inside the substantially rectangular housing at or near the distal end of the catheter tip.

22. The steerable catheter according to claim 21,
wherein the tool channel has a tool channel diameter centered about a catheter axis.

23. The steerable catheter according to claim 1,
wherein the catheter body includes a proximal section attachable to an actuator unit and a distal section insertable into a lumen of a patient, the distal section of the catheter body having a plurality of bending segments, and
wherein each bending segment is connected to the actuator unit by at least one drive wire arranged along a wall of the catheter body, and
wherein the at least one drive wire attached to each bending segment is configured to transfer an actuating force from the actuator unit to the catheter body so as to steer the catheter tip to a position and/or orientation within the lumen.

24. The steerable catheter according to claim 23,
wherein, when the catheter tip is steered by the actuation force, the at least one flat side-surface of the housing interlocks with the ramp-like surface such that a position and/or orientation of the imaging device remains substantially unchanged with respect to the position and/or orientation of the catheter tip.

25. A steerable catheter comprising:
a catheter body having a catheter tip and a tool channel spanning from a proximal end of the catheter body and through the catheter tip along a catheter axis, the tool channel configured to receive a housing therein, wherein:
the catheter tip includes a ramp-like surface;
the ramp-like surface is an inclined flat surface formed at an angle with respect to a plane that is substantially parallel to the catheter axis, such that a cross-section of the angle increases to a full diameter as the ramp-like surface spans from a distal end towards a proximal end of the catheter tip;
one side-surface of the housing is configured to mate with the ramp-like surface;
an opening of the distal end of the catheter tip is substantially oval shaped, with at least one flat surface; and
mating of the at least one side-surface of the housing with the ramp-like surface prevents rotation of the housing with respect to the tool channel.

* * * * *